(12) United States Patent
Walshe

(10) Patent No.: US 8,801,754 B2
(45) Date of Patent: Aug. 12, 2014

(54) TISSUE ANCHOR SYSTEM

(76) Inventor: Christopher Walshe, Portsmouth, VA (US)

( * ) Notice: Subject to any disclaimer, the term of this patent is extended or adjusted under 35 U.S.C. 154(b) by 234 days.

(21) Appl. No.: 12/573,631

(22) Filed: Oct. 5, 2009

(65) Prior Publication Data

US 2010/0022822 A1    Jan. 28, 2010

Related U.S. Application Data

(60) Continuation of application No. 11/435,339, filed on May 16, 2006, now abandoned, which is a division of application No. 10/324,392, filed on Dec. 18, 2002, now Pat. No. 7,056,333, which is a continuation of application No. 09/716,851, filed on Nov. 17, 2000, now Pat. No. 6,506,190, which is a continuation of application No. PCT/US99/11225, filed on May 21, 1999.

(60) Provisional application No. 60/086,284, filed on May 21, 1998.

(51) Int. Cl.
*A61B 17/04* (2006.01)

(52) U.S. Cl.
USPC .............................. 606/232; 600/37; 606/142

(58) Field of Classification Search
USPC ................ 606/139, 151, 232; 600/37, 29, 30; 623/23.72
See application file for complete search history.

(56) References Cited

U.S. PATENT DOCUMENTS

| 4,244,689 A | 1/1981 | Ashman |
| 4,424,811 A | 1/1984 | Groot |
| 4,669,473 A | 6/1987 | Richards et al. |
| 4,738,255 A | 4/1988 | Goble et al. |
| 4,828,562 A * | 5/1989 | Kenna ........................ 623/13.13 |
| 4,898,156 A | 2/1990 | Gatturna et al. |
| 4,931,042 A | 6/1990 | Holmes et al. |
| 4,950,284 A | 8/1990 | Green et al. |
| 5,013,292 A * | 5/1991 | Lemay ............................ 600/30 |
| 5,127,412 A * | 7/1992 | Cosmetto et al. ............. 128/898 |
| 5,217,486 A | 6/1993 | Rice et al. |
| 5,269,783 A | 12/1993 | Sander |
| 5,330,501 A | 7/1994 | Tovey et al. |
| 5,333,624 A | 8/1994 | Tovey |
| 5,354,298 A | 10/1994 | Lee et al. |
| 5,354,305 A | 10/1994 | Lewis, Jr. et al. |
| 5,368,595 A | 11/1994 | Lewis |
| 5,368,599 A | 11/1994 | Hirsch et al. |
| 5,374,268 A | 12/1994 | Sander |
| 5,380,334 A | 1/1995 | Torrie et al. |
| 5,382,257 A | 1/1995 | Lewis et al. |

(Continued)

FOREIGN PATENT DOCUMENTS

EP    0558993    9/1993
EP    1159920    5/2001

(Continued)

*Primary Examiner* — Corrine M McDermott
*Assistant Examiner* — Alexander Orkin
(74) *Attorney, Agent, or Firm* — Jones Walker LLP

(57) ABSTRACT

A suburethral sling system including a suburethral sling body having first and second ends; a tissue anchor connected approximate to each of the first and second sling ends, the tissue anchors having barbs for retaining the anchors in soft tissue; and an anchor delivery device having a hand-grip and an anchor stay adapted to reversibly mate with the tissue anchors.

9 Claims, 19 Drawing Sheets

(56) References Cited

U.S. PATENT DOCUMENTS

| | | | |
|---|---|---|---|
| 5,383,905 A | 1/1995 | Golds et al. | |
| 5,447,417 A | 9/1995 | Kuhl et al. | |
| 5,458,601 A * | 10/1995 | Young et al. | 606/232 |
| 5,474,518 A * | 12/1995 | Farrer Velazquez | 600/30 |
| 5,478,345 A | 12/1995 | Stone et al. | |
| 5,480,403 A | 1/1996 | Lee et al. | |
| 5,496,371 A | 3/1996 | Eppley et al. | |
| 5,500,000 A | 3/1996 | Feagin et al. | |
| 5,501,695 A | 3/1996 | Anspach, Jr. et al. | |
| 5,507,754 A | 4/1996 | Green et al. | |
| 5,549,617 A | 8/1996 | Green et al. | |
| 5,554,194 A | 9/1996 | Sanders | |
| 5,562,689 A | 10/1996 | Green et al. | |
| 5,584,835 A | 12/1996 | Greenfield | |
| 5,626,597 A | 5/1997 | Urban et al. | |
| 5,641,502 A | 6/1997 | Skalla et al. | |
| 5,643,274 A | 7/1997 | Sander et al. | |
| 5,643,319 A | 7/1997 | Green et al. | |
| 5,645,588 A | 7/1997 | Graf et al. | |
| 5,660,185 A | 8/1997 | Shmulewitz et al. | |
| 5,676,008 A | 10/1997 | Morin | |
| 5,700,270 A | 12/1997 | Peyser et al. | |
| 5,702,398 A * | 12/1997 | Tarabishy | 606/232 |
| 5,720,766 A | 2/1998 | Zang et al. | |
| 5,728,136 A | 3/1998 | Thal | |
| 5,776,110 A | 7/1998 | Guy | |
| 5,800,445 A | 9/1998 | Ratcliff et al. | |
| 5,807,403 A | 9/1998 | Beyar et al. | |
| 5,824,011 A | 10/1998 | Stone et al. | |
| 5,893,856 A | 4/1999 | Jacob et al. | |
| 5,938,667 A | 8/1999 | Peyser et al. | |
| 5,948,000 A | 9/1999 | Larsen et al. | |
| 5,948,001 A | 9/1999 | Larsen | |
| 5,954,057 A * | 9/1999 | Li | 128/898 |
| 5,957,888 A | 9/1999 | Hinchliffe | |
| 5,957,953 A | 9/1999 | DiPoto et al. | |
| 5,968,078 A | 10/1999 | Grotz | |
| 5,972,000 A | 10/1999 | Beyar et al. | |
| 5,976,127 A | 11/1999 | Lax | |
| 5,997,552 A | 12/1999 | Person et al. | |
| 6,027,523 A | 2/2000 | Schmieding | |
| 6,042,583 A | 3/2000 | Thompson et al. | |
| 6,053,935 A | 4/2000 | Brenneman et al. | |
| 6,063,088 A | 5/2000 | Winslow | |
| 6,086,608 A * | 7/2000 | Ek et al. | 606/232 |
| 6,190,401 B1 | 2/2001 | Green et al. | |
| 6,334,446 B1 | 1/2002 | Beyar | |
| 6,506,190 B1 | 1/2003 | Walshe | |
| 6,592,593 B1 | 7/2003 | Parodi et al. | |
| 6,666,872 B2 | 12/2003 | Barreiro et al. | |
| 6,691,711 B2 | 2/2004 | Raz et al. | |
| 7,056,333 B2 | 6/2006 | Walshe | |
| 2004/0059344 A1 | 3/2004 | Parodi et al. | |

FOREIGN PATENT DOCUMENTS

| | | |
|---|---|---|
| FR | 2750031 | 12/1997 |
| WO | 9707743 | 3/1997 |
| WO | 9729693 | 8/1997 |

\* cited by examiner

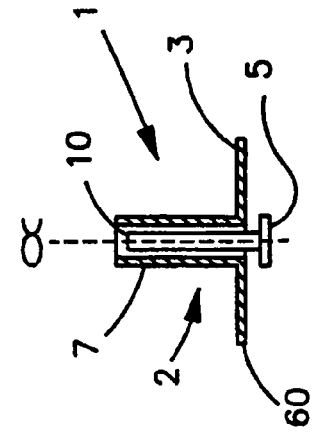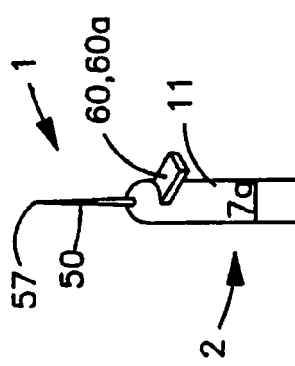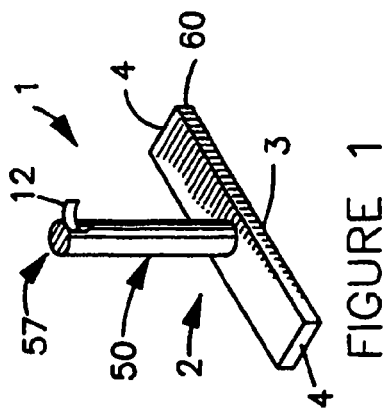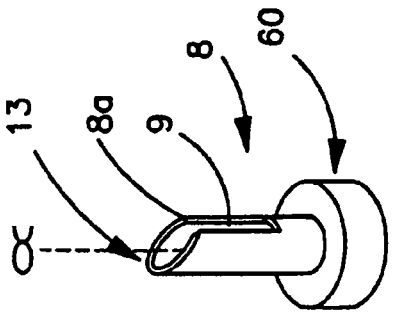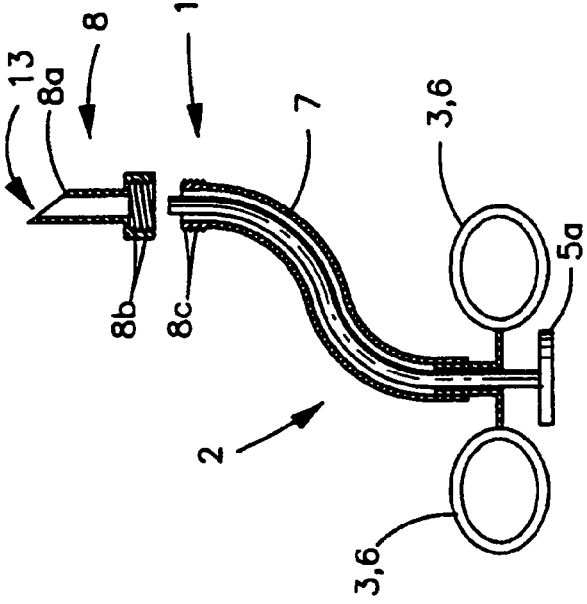

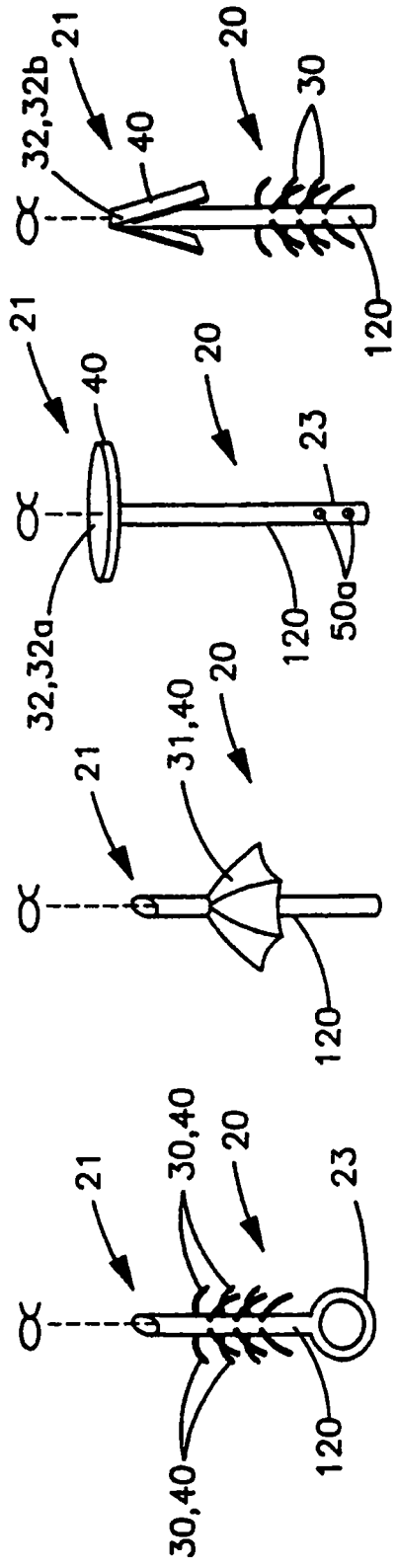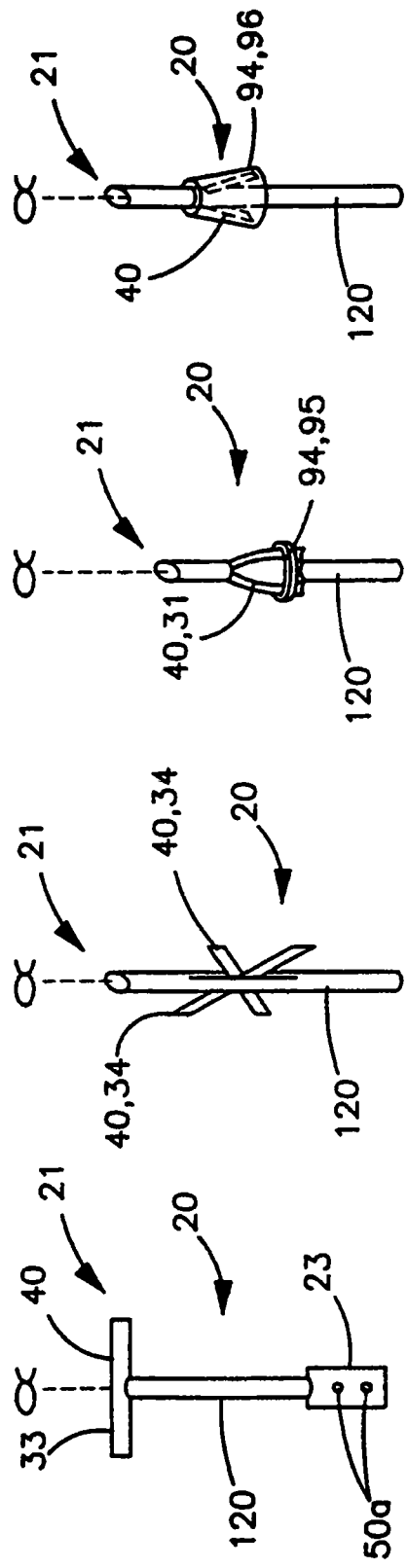

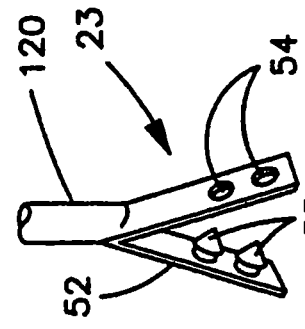
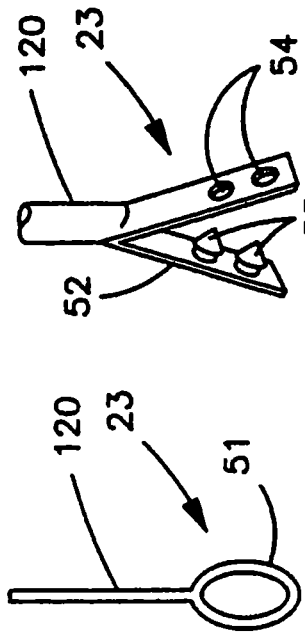
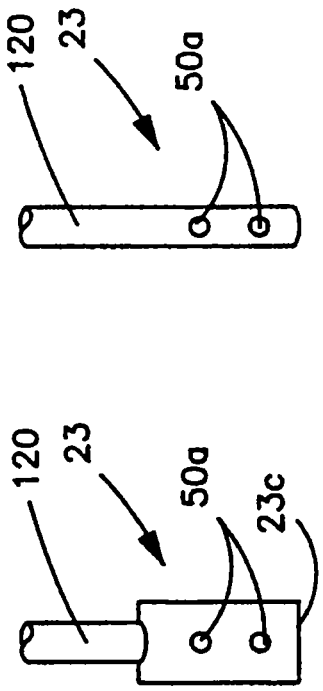
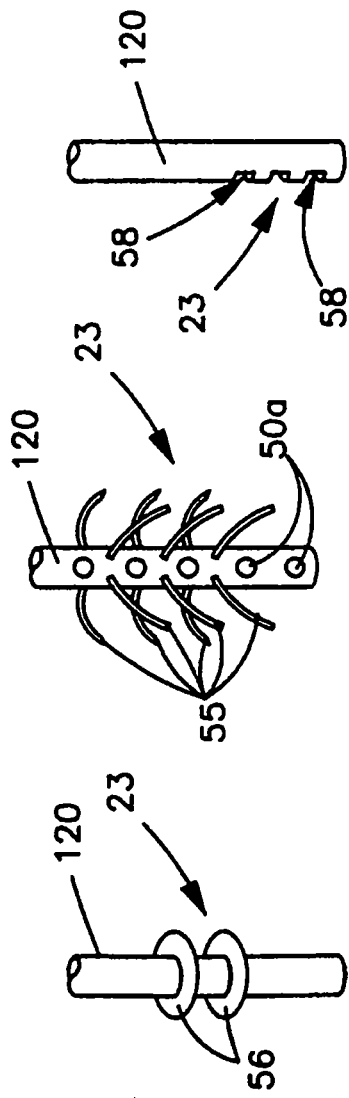
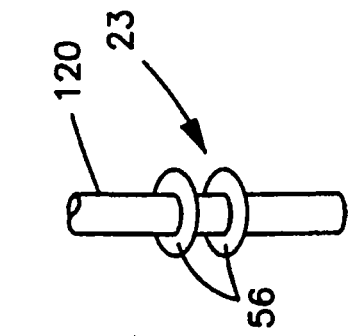

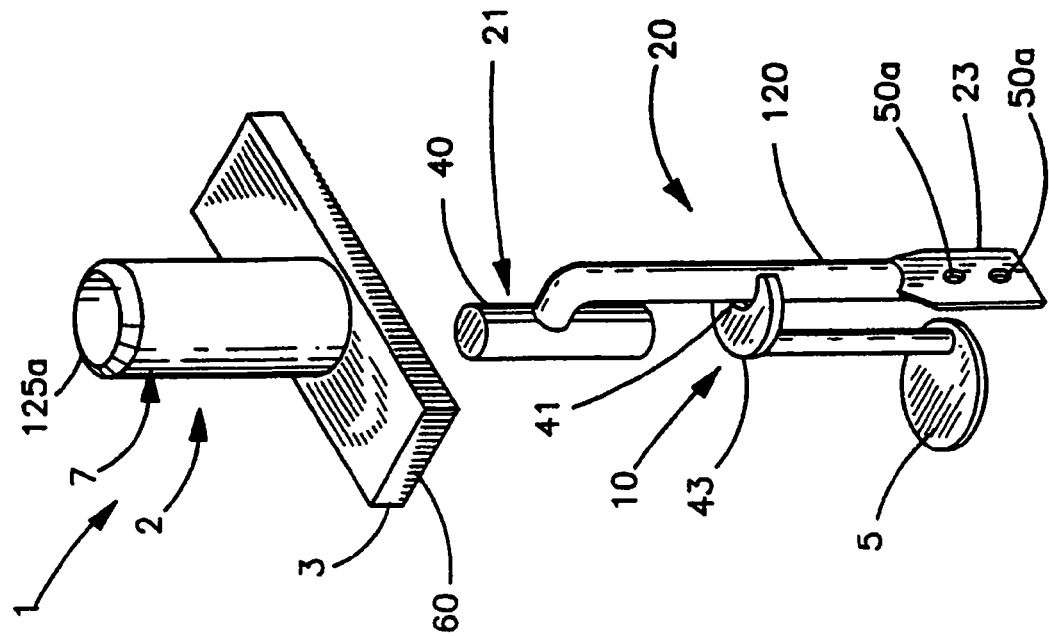
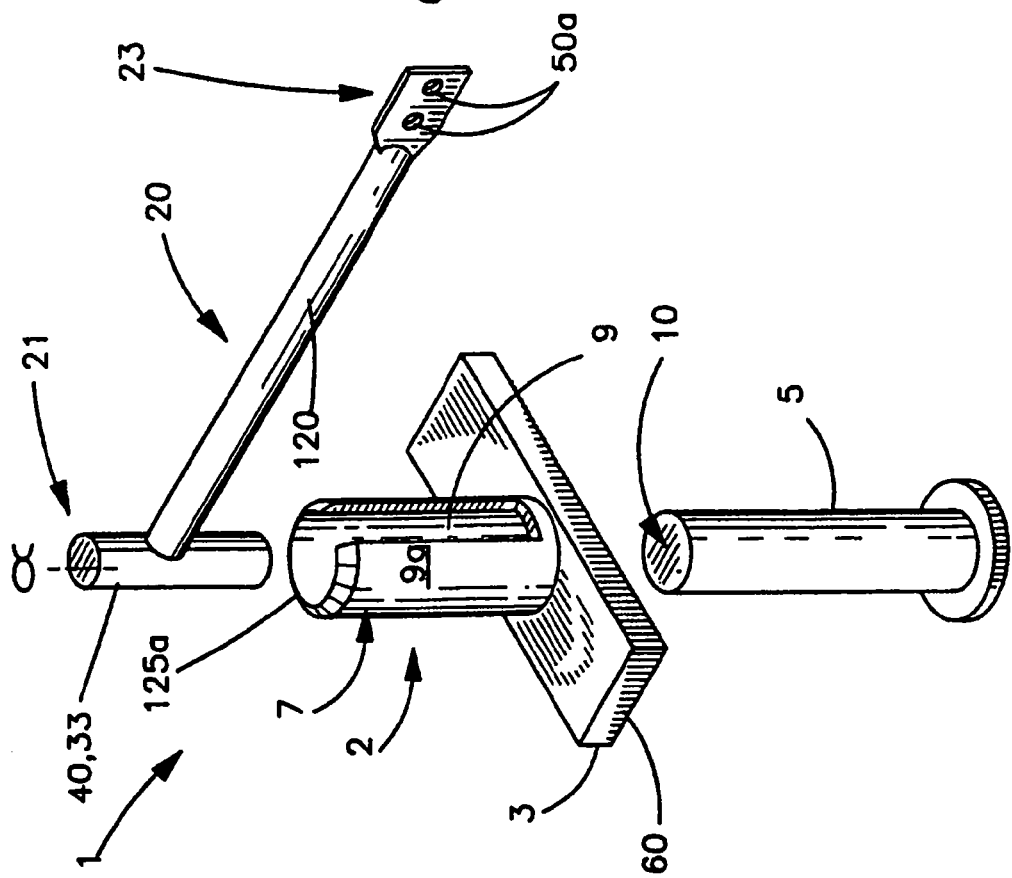

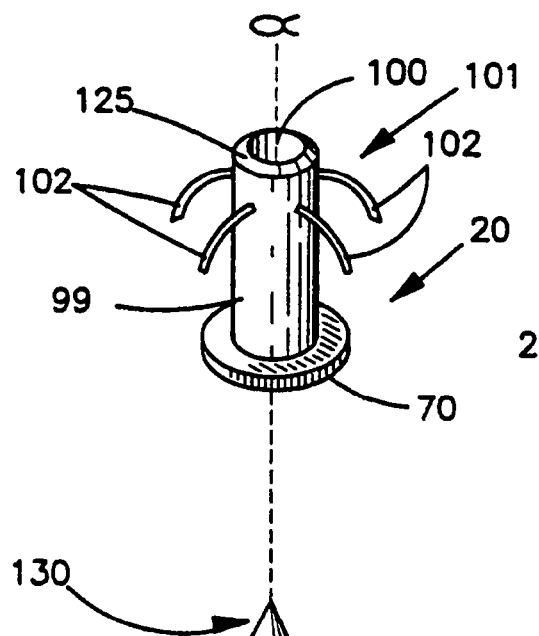
FIGURE 8b
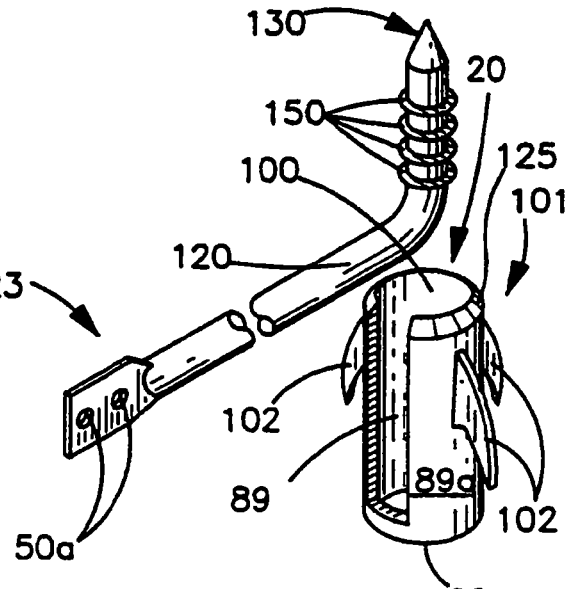
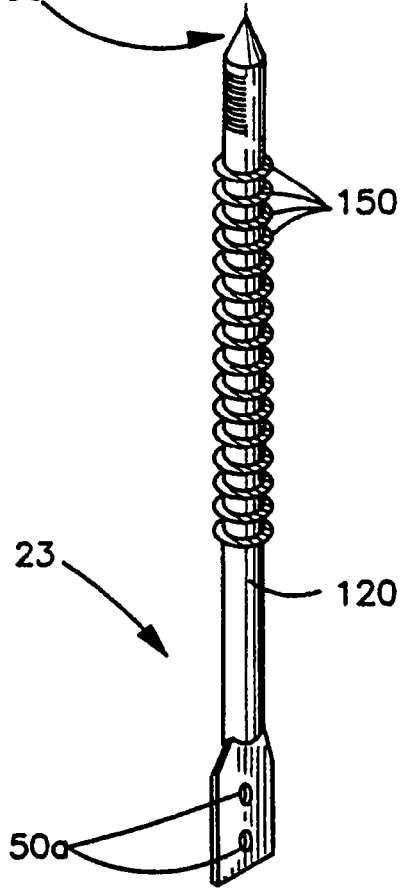
FIGURE 8a
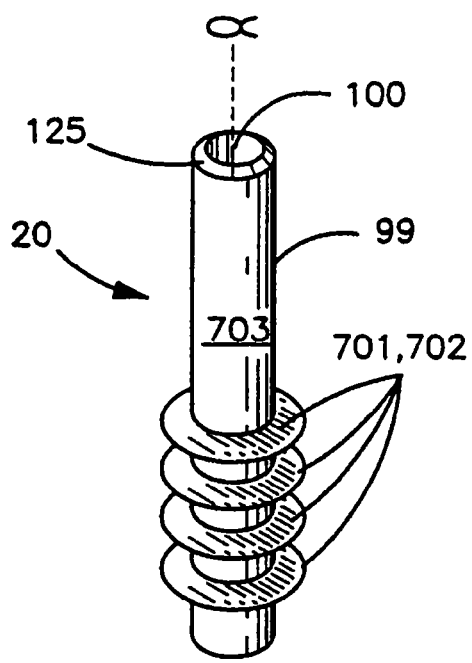
FIGURE 8c

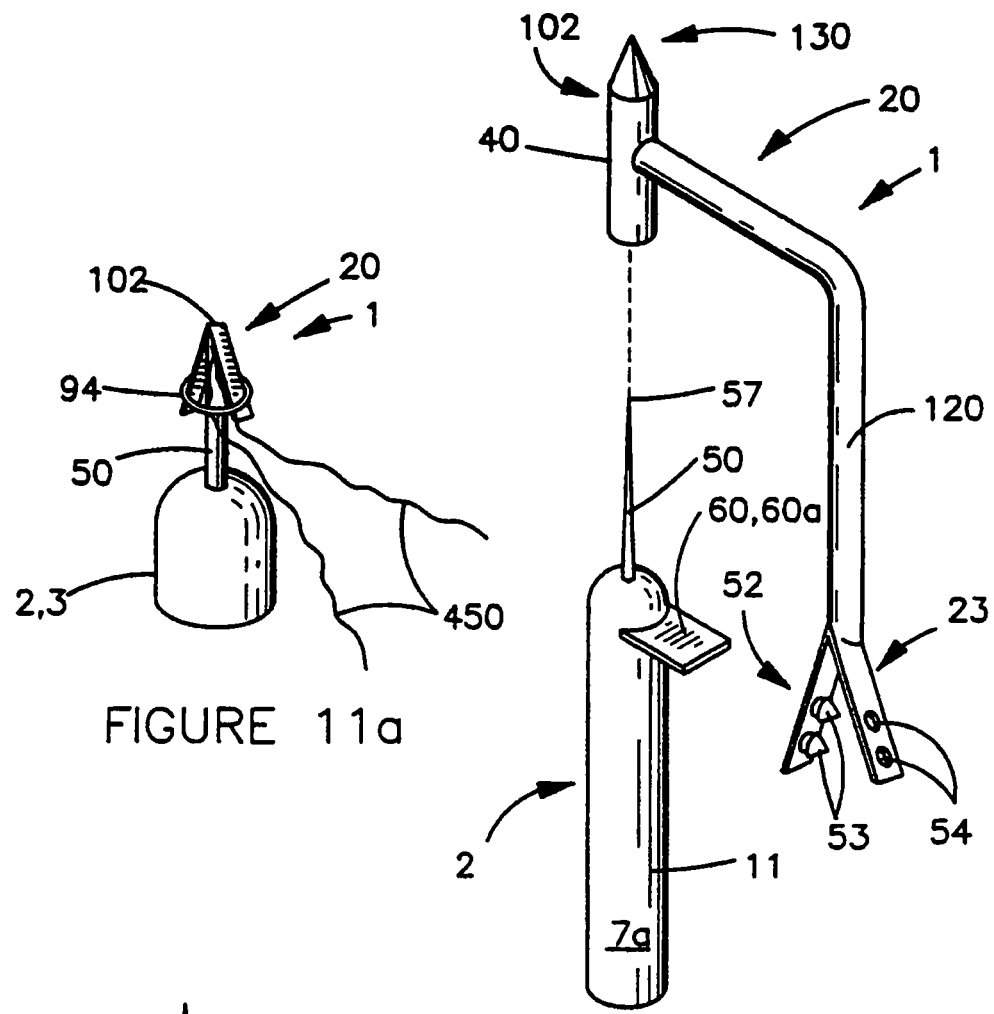
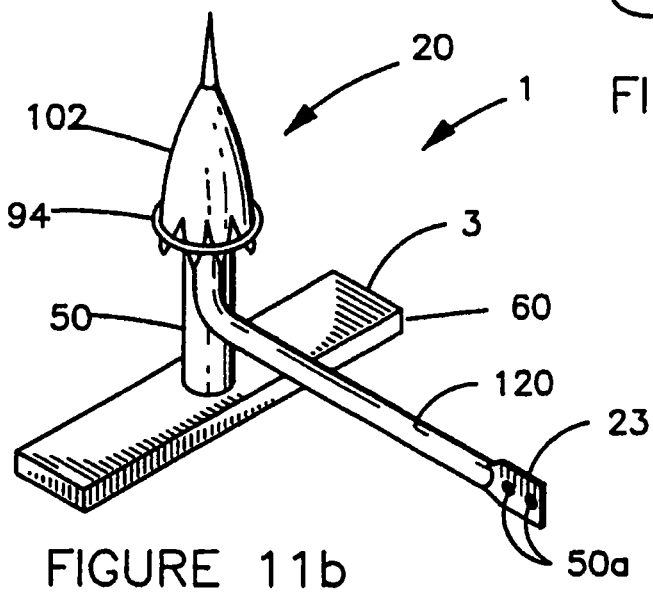
FIGURE 11a
FIGURE 11b
FIGURE 11c

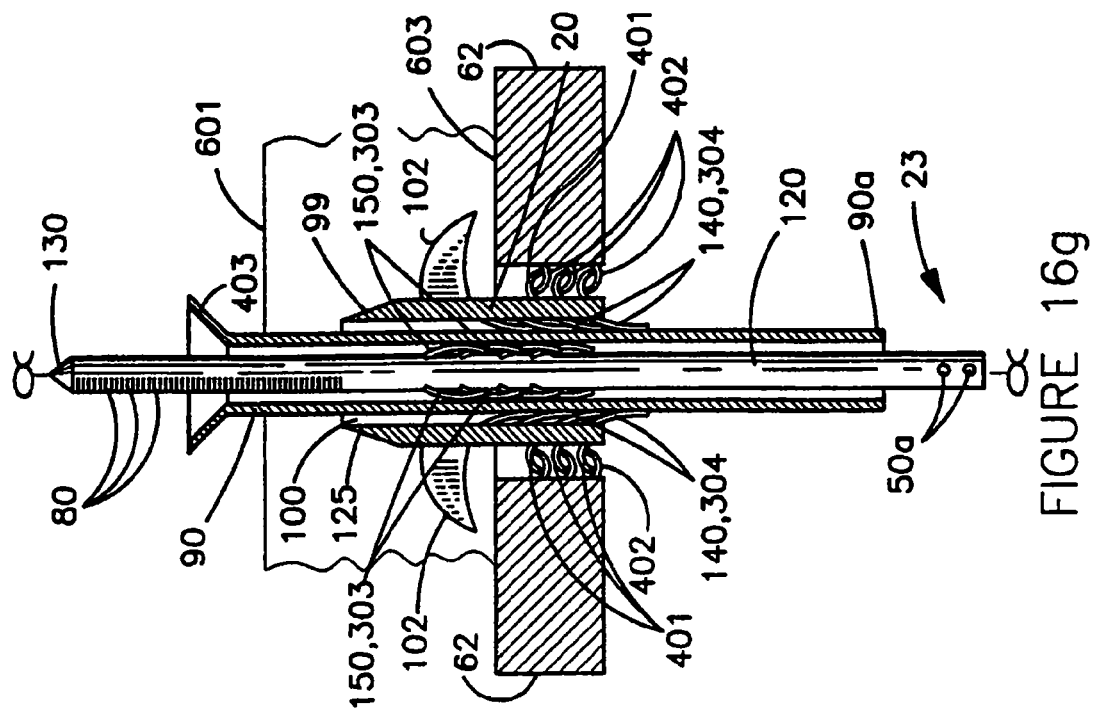
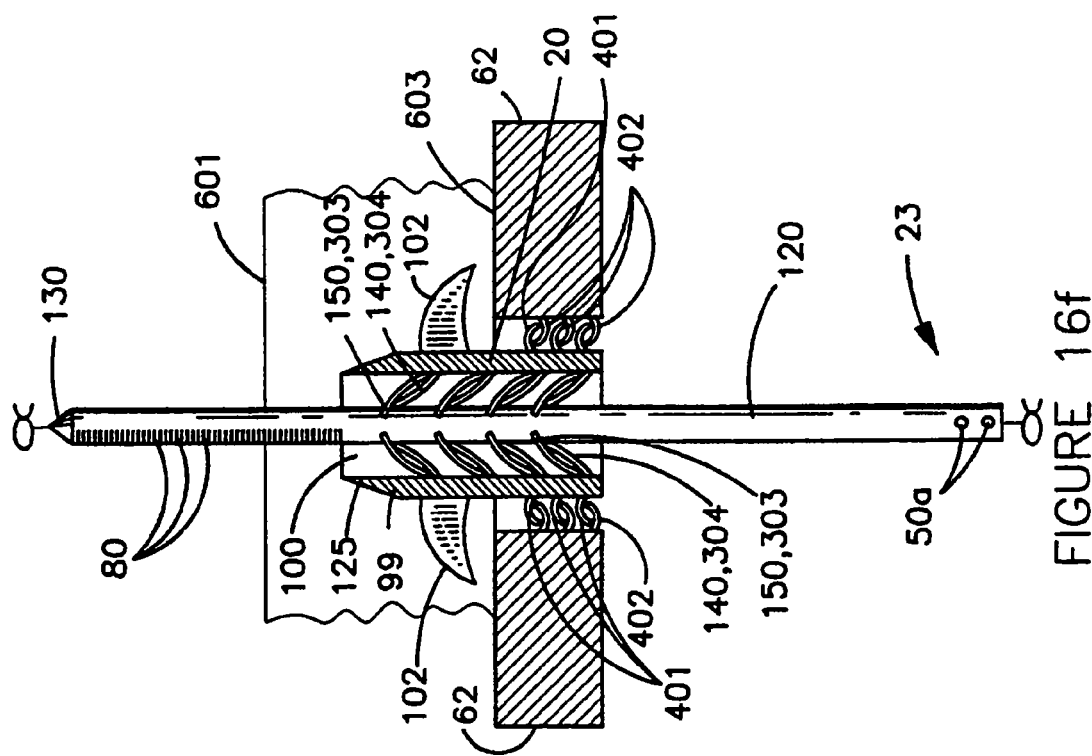

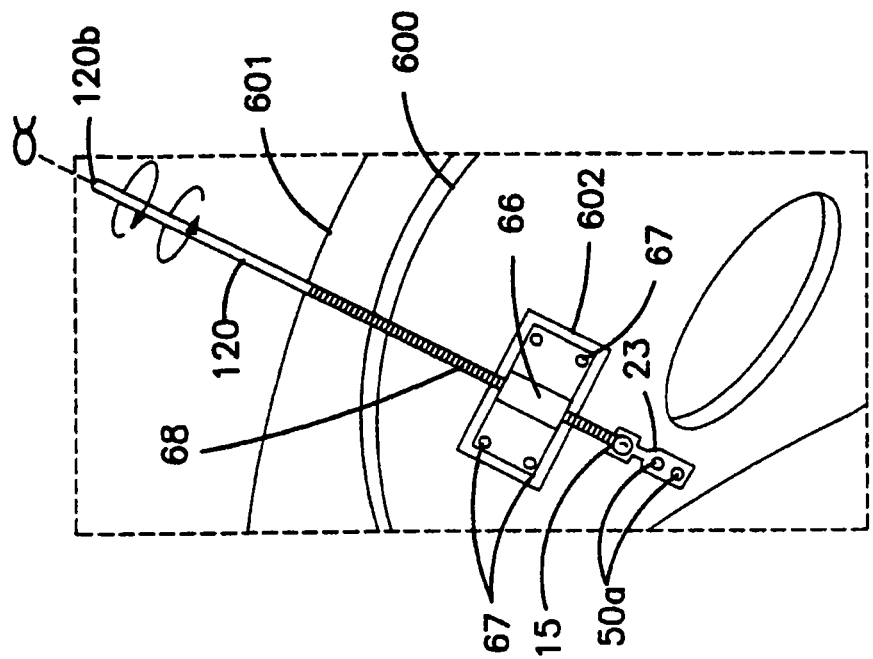
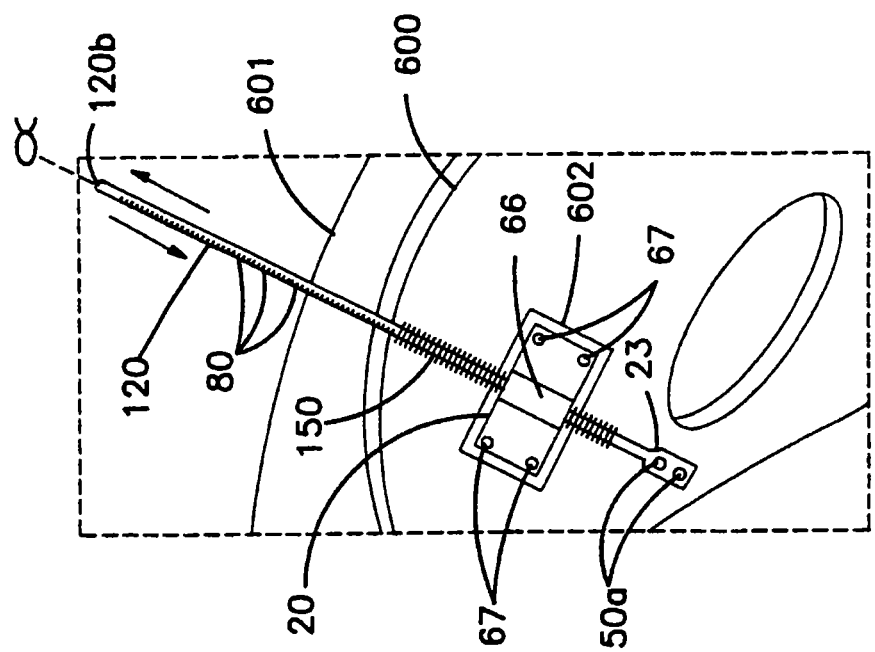

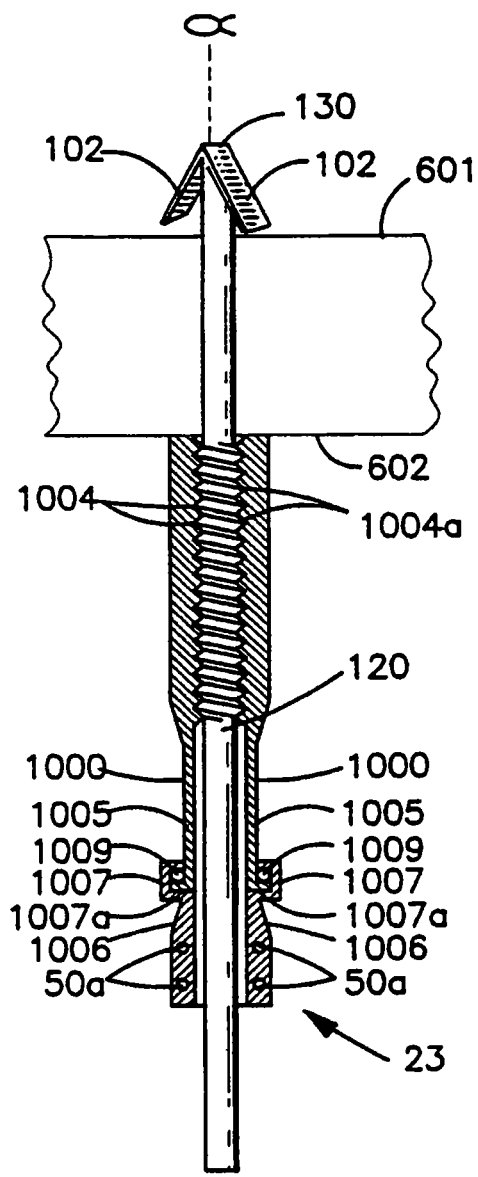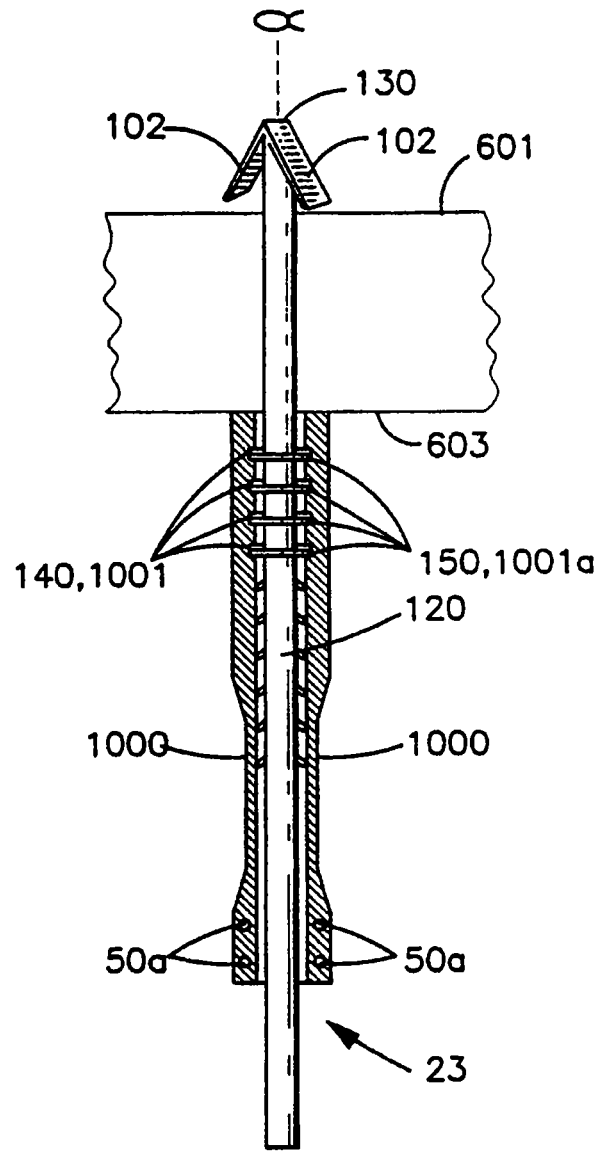
FIGURE 19a
FIGURE 19b

TISSUE ANCHOR SYSTEM

PRIORITY CLAIM

This application is a continuation of U.S. patent application Ser. No. 11/435,339, now abandoned, filed on May 16, 2006, which is a divisional of U.S. patent application Ser. No. 10/324,392, filed on Dec. 18, 2002, now U.S. Pat. No. 7,056,333, which is a continuation of U.S. patent application Ser. No. 09/716,851, filed on Nov. 17, 2000, now U.S. Pat. No. 6,506,190, which claims priority to International Application number PCT/US99/11225, which was filed on May 21, 1999, and which claims priority to U.S. Provisional Application No. 60/086,284, filed on May 21, 1998, all of which are incorporated by reference herein in their entirety

BACKGROUND ART

One problem this invention intends to address is urinary incontinence, but the invention is applicable to a broader range of problems. The background, however, will discuss urinary incontinence as an example.

Urinary incontinence is an involuntary release of urine when increases in abdominal pressure, caused by sneezing, coughing, or exercising, are not uniformly transmitted to the proximal urethra, resulting in urine "leakage." Moderate stress urinary incontinence ("SUI") is inconvenient and can be a social and hygienic problem, while severe SUI can be disabling. SUI occurs in women and is caused by either hypermobility of the bladder neck and proximal urethra (excessive downward and rotational movement of the bladder neck) or intrinsic sphincter deficiency.

Several defects can result in loss of support of the bladder neck. Examples of these defects are: (a) breakage or abnormal stretching of the passive supports of the bladder and urethra (those connective tissues supporting these structures); or (b) loss of the active support of the bladder neck, vagina, and rectum provided by the levator ani muscle. For instance, one example of passive support failure is paravaginal "defects" caused by separation of the vaginal wall from the pelvis caused by breakage or stretching of connective tissue (pelvic organ prolapse). Such separation results in downward rotation of the vaginal wall, which in turn results in downward rotation of the bladder neck because the bladder is partially supported by the vagina. An example of loss of active support is loss of muscle tone in the levator ani muscle. This muscle operates as a floor, or platform, supporting the bladder during standing and normal activity. Normal muscle tone of the levator ani relieves the passive support of the pressures caused by overlaid abdominal viscera. Loss of muscle tone may result in downward rotation of the bladder.

Treatment of SUI caused by hypermobility of the bladder and proximal urethra requires supporting the bladder neck, generally at the urethrovesical junction ("UVJ"). Correction requires support of the UVJ area, which helps balance increased abdominal pressures and which allows the bladder neck to properly compress and close in response to increased pressures, thus preventing urine leakage. Support may be provided in various surgical procedures, including anterior colporrhaphy, retropubic urethropexy, vaginal needle urethropexy, and suburethral sling procedures.

One particular type of surgery is briefly discussed-retropubic urethropexy ("RU"). In RU, a series of sutures are used to support the UVJ. The ends of the sutures attach at various points in the body cavity depending upon the type of failure (loss of active support, failure of a portion of passive connective tissue, etc.). The sutures support and properly elevate the bladder neck at the UVJ to maintain the compressibility and pliability of the urethra and to avoid compromising the urethral sphincteric mechanism.

In various RU procedures, different anchoring tissues are used to support the sutures. These anchoring tissues include, but are not limited to, soft tissues such as pubocervical fascia, pubourethral ligaments, Cooper's ligaments, and rectus fascia. One RU procedure, generally known as the Marshall-Marchetti-Kantz procedure, uses several sutures, with the one end of each suture being attached to the vaginal wall adjacent to the urethra straddling the UVJ bilaterally. The opposite suture end passes through the retropubic periosteum.

In another RU procedure, known as the Burch procedure, the first end of a series of sutures is positioned in both sides of the vagina wall (straddling the urethra) below Cooper's Ligament 602, and the other end of the sutures is positioned in Cooper's Ligament 602, thereby supporting the vaginal wall and the UVJ.

RU procedures generally support an area by using sutures, and additional support is provided by using slings (either man-made materials or tissue grafted material) placed under the area to be supported and sutured into an anchoring tissue, such as in suburethral sling procedures (e.g. a Goebell-Stoeckel procedure).

Problems associated with surgical correction of the failed support mechanisms include under- or over-correction of the UVJ. The surgeon must determine the degree of support necessary to properly elevate and support the UVJ to properly address the SUI problem. This determination must be made both pre- and intra-operatively. Too little elevation causes SUI to remain, although the degree of SUI may be reduced. Too much elevation can result in voiding dysfunction (reduced capacity or inability to void), prolonged catheterization, and the need for postoperative correction.

The incidence of postoperative urinary retention can be as high as 30% at two weeks after surgery, and 5% of patients have postoperative urinary retention that persists. Many patients with less severe cases of postoperative obstructive symptoms also benefit greatly. Symptomatic detrusor instability represents the bladder's response to increased outlet resistance caused by an improperly tensioned sling. The incidence of postoperative irritative symptoms secondary to detrusor instability can be as high as 20%. Appropriate tensioning of the sling minimizes persistent incontinence and voiding dysfunction.

Generally, all of the above procedures require placement of sutures into an anchoring tissue or tissues and may also require placement of sutures into supporting devices, such as slings. Placement is provided through suturing needles, either straight or arcuate, or the use of needle suturing devices, such as push and catch systems, or non-adjustable fascial attachment systems. The suture placement in the tissue can be completely through the tissue or partially through the tissue.

SUMMARY OF THE INVENTION

Accordingly, the invention is a tissue anchoring system, including a tissue anchoring device and tissue anchors. At least one embodiment of the tissue anchoring system will be used in soft tissue. The tissue-anchoring device includes housing and a tissue anchor. The tissue anchor is placed on the tissue-anchoring device that is advanced into a tissue. The device may optionally have a plunger assembly slidably positioned in the housing to assist advancing the anchor into a tissue. The tissue anchor has a barb end and a shaft. The barb end is adapted to resist removal from a tissue after it is inserted. The tissue anchor shaft and the barb end may be hollow. The shaft of the anchor has an attachment member distal from the barb end so that the attachment member may attach directly to tissue or attach to tissue using sutures or a sling. The tissue anchors may be adjustable.

DISCLOSURE OF THE INVENTION

It is an object of the invention to provide a tissue-anchoring device that does not require suturing to attach to tissue.

It is an object of the invention to provide a tissue-anchoring device that may be repeatedly reloaded with anchors.

It is an object of the invention to provide a tissue-anchoring device that may insert completely through a tissue or partially through a tissue.

It is an object of the invention to provide an alternative to sutures in relatively inaccessible areas.

It is an object of the invention to provide a tissue-anchoring device that can be hand-held or used with endoscopic surgery techniques and devices, especially flexible endoscopes.

It is an object of the invention to provide an adjustable tissue-anchoring device to adjust the placement of devices or tissues attached to the anchor postoperatively without further invasive surgery.

It is an object of the invention to provide an adjustable tissue-anchor device attachable to tissue using sutures or staples when a surgeon deems it more suitable.

DESCRIPTION OF THE DRAWINGS

FIG. 1 illustrates an embodiment of a tissue-anchor delivery device.

FIG. 1a illustrates another embodiment of a tissue-anchor delivery device.

FIG. 2 illustrates another embodiment of a tissue-anchor delivery device having a plunger with the delivery device shown as a cross-section.

FIG. 3a illustrates a thimble-like embodiment of a tissue-anchor delivery device.

FIG. 3b illustrates another embodiment of a tissue-anchor delivery device that may be used in connection with an endoscope wherein the delivery device is shown in cross-section to illustrate the plunger positioned therein.

FIG. 3c illustrates the configuration of the tip used in connection with the tissue-anchor delivery device shown in FIG. 3b.

FIG. 4a illustrates an anchor having a ringed attachment member and finger projections for a barb.

FIG. 4b illustrates an anchor having an umbrella-like barb.

FIG. 4c illustrates an anchor having an attachment member a disk barb and an attachment member comprising holes.

FIG. 4d illustrates an anchor having an arrow shaped barb and finger-like barbs.

FIG. 4e illustrates an anchor having a T-shaped barb having holes in the attachment member.

FIG. 4f illustrates an anchor having a star-shaped barb.

FIG. 4g illustrates the anchor shown in FIG. 4b having a barb retaining device in the form of a collar positioned over the umbrella-shaped barb.

FIG. 4h illustrates another barb retaining device, namely a sleeve positioned over the barb.

FIG. 6a illustrates an embodiment of an attachment member having holes extending therethrough.

FIG. 6b illustrates another embodiment of an attachment member wherein holes are configured with a tab near the bottom of the shaft.

FIG. 6c illustrates another embodiment incorporating a ring-shaped attachment member.

FIG. 6d illustrates another embodiment of an attachment member in the form of a clamp.

FIG. 6e illustrates another embodiment of an attachment member comprising finger-like projections and holes.

FIG. 6f illustrates another embodiment of an attachment member having annular projections positioned on the shaft.

FIG. 6g illustrates another embodiment of an attachment member having indentations configured in the shaft.

FIG. 7a illustrates an embodiment of the delivery device having a plunger and using a T-shaped anchor.

FIG. 7b illustrates another embodiment of the delivery device having a plunger with a disc-like end designed to engage the shaft of the anchor and anchor head.

FIG. 8a illustrates an embodiment of an adjustable tissue-anchoring device.

FIG. 8b illustrates another embodiment of an adjustable tissue-anchoring device.

FIG. 8c illustrates another embodiment of an anchor body with the barbs removed and having annular projections thereon to engage a retaining device.

FIG. 11a illustrates an embodiment of a thimble-shaped delivery device wherein sutures are attached near the barb.

FIG. 11b illustrates another embodiment of a delivery device.

FIG. 11c illustrates another embodiment of a delivery device having a pen-shaped housing.

FIGS. 16a-16g illustrate the steps of placement of an adjustable anchor and shaft within a tissue. In each FIGS. 16a-16g, the plunger, anchor body, the sleeve, and the adjuster cylinder are shown as cross-sections. The shaft and interleaving members are shown in full view against those cross-sections.

FIG. 18b illustrates a close-up view of the embodiment in FIG. 18a.

FIG. 18c illustrates a close-up view of the embodiment in FIG. 18a wherein corresponding threads are configured on the shaft and housing to allow the shaft to be adjustable.

FIG. 19a illustrates a cross-sectional view of another embodiment of the invention wherein the shaft and attachment member are not connected, and wherein the ratcheting device comprises corresponding threads positioned on the housing and on the shaft. FIG. 19a also illustrates the attachment member as rotatable about the housing. The shaft is shown in full view, and an attachment member is shown operatively attached to the housing.

FIG. 19b illustrates an embodiment similar to that shown in FIG. 19a wherein the ratcheting device on the shaft comprises annular projections. The shaft is shown in full view.

BEST MODE FOR CARRYING OUT THE INVENTION

Figure 5A:
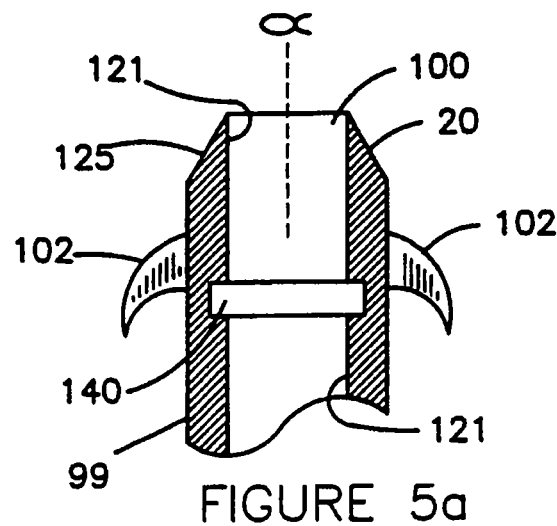
FIG. 5a illustrates an embodiment of an anchor having a ratcheting device configured therein as a groove.

Illustrations of construction, design, and methods of operation of the invention are set forth below with specific references to the Figures. However, it is not the intention of the inventor that the slope of his invention be limited to these embodiments.

FIG. 1 illustrates one embodiment of the tissue-anchor delivery device 1. Delivery device 1 comprises a housing 2 and one or more finger grips 3, which comprise flats 4 on opposing sides of housing 2 designed to enable a surgeon to hold device 1. Finger grips 3 may be rings 6 (see FIG. 3b) through which the surgeon inserts fingers, a thimble (see FIG. 3a), a handgrip, or any other shape that enables a surgeon to hold delivery device 1. Finger grips 3 are unnecessary if housing 2 is adapted to be hand-held, such as a pen-shaped housing 11 shown in FIG. 1a.

FIGS. 1a and 3a illustrate an anchor stay 50. Anchor stay 50 comprises a portion of housing 2 adapted to retain an anchor 20 (not shown) thereto, as described below. In the embodiment shown in FIG. 3a, anchor 20 (not shown) will slip over anchor stay 50, while in the embodiment shown in FIG. 1, anchor 20 will clip onto stay 50 using clip member 12.

Anchor stay 50 is a rigid projection extending away from the plane of the finger grip flats 4. Anchor stay 50 may have a clip member 12 positioned near tip 57 to removably couple anchor 20 to stay 50. Clip member 12 may include a compression-fit C-type ring for gripping the shaft of an anchor 20. Anchor stay tip 57 may also be designed to reversibly mate with an anchor 20 that is positioned on or against tip 57.

Alternatively, as shown in FIG. 2, delivery device 1 may include a plunger 5 slidably positioned in hollow barrel portion 7 of housing 2 and operated by a surgeon. Plunger 5 has an anchor end 10 adapted to engage an anchor 20. Anchor end 10 may be a flat end to push anchor 20, a pointed end adapted to engage a hollow shaft portion of an anchor 20 (see FIGS. 3a and 11c), a clip member 12 (see FIG. 1) positioned on end 10 designed to couple to anchor 20. Though not shown, clip member 12 may alternatively be positioned on anchor shaft 120 (seen in FIGS. 4a-4h). Anchor end 10 can have any structure engaging anchor 20 that allows plunger 5 to advance anchor 20 into a tissue and uncouple therefrom, leaving anchor 20 in tissue.

Other embodiments of delivery device 1 are shown in FIGS. 3a and 3b. These embodiments also comprise a housing 2 and finger grip(s) 3. As shown in FIG. 3a, housing 2 and finger grips 3 comprise a thimble 3a, while FIG. 3b shows finger grips 3 as rings 6. Viewing FIG. 3b, housing 2 has a flexible hollow barrel portion 7. A flexible plunger 5a is slidably positioned in hollow barrel portion 7, which comprises a sleeve within which flexible plunger 5a slides. This embodiment is suitable where the invention will be used in conjunction with an endoscope or in anatomic areas that are hard to reach manually with a rigid device. Hollow barrel portion 7 may be rigid, but is preferable flexible so that it may be used in conjunction with an endoscope. The hollow barrel portion 7 length may range from ¼-inch to one or more feet, depending upon the particular application, and the length of flexible plunger 5a is constructed accordingly.

Viewing FIG. 3b, hollow barrel portion 7 has a detachable tip 8. Tip 8 screws onto hollow barrel portion 7 using corresponding threads 8b, 8c which allows a surgeon to change tips 8. Viewing FIG. 3c, tip 8 has a knife-edge 13 to penetrate tissue. Tip 8 may have a slot 9 starting at the edge 8a of tip 8 and extending down tip 8, substantially along the longitudinal axis a shown in FIG. 3c.

Viewing FIG. 1a, delivery device 1 may also comprise a stop 60, shown as an outwardly projecting ridge 60a, that is shown located on the external walls 7a of the hollow barrel portion 7 in FIG. 1a. Ridge 60a controls the extent of insertion of hollow barrel portion 7. Alternatively, viewing FIG. 1, finger grips 3 can act as stop 60. The need for a separate delivery device 1 may be eliminated if anchor 20, later described, is itself constructed to guide the placement of anchor 20 into tissue by hand.

As shown in FIGS. 4a-f, anchor 20 can have a wide variety of shapes depending upon the application. Anchor 20 has a barb end 21 and a shaft 120 and may also comprise an attachment member 23 (see FIGS. 4a, 4c, and 4e) positioned on shaft 120 distal from barb end 21. Inclusion of shaft 120 is optional. Please note that in later embodiments, the anchor shaft is also referred to as shaft 120 (e.g. FIGS. 16a-16g). Viewing FIG. 1a, if anchor 20 lacks shaft 120, attachment member 23, later described, should be placed on barb end 21 (not shown), or the sutures 450 should directly attach to barb 102. Shaft 120 may be from ¼ inch to a foot or more in length, depending upon the application.

Viewing FIG. 4a, barb end 21 is adapted to resist removal of anchor 20 after anchor 20 has been inserted in or through a tissue and anchored by barb 40. For example, barb 40 may comprise: a series of downwardly-pointing fingers 30 (also referred to as wing-like projections 30) (see FIG. 4a); a downwardly-pointing conical umbrella 31 (see FIG. 4b); a flat area 32, such as a disk 32a (see FIG. 4c) or an arrow end 32b (see FIG. 4d); a T-shaped head 33 (see FIG. 4e); a star-shaped head 34 (see FIG. 4f); or any other head shape that will resist removal of anchor 20 from tissue. Barb 40 may be flexible or collapsible, such as the umbrella 31 shown in FIG. 4b. Preferably, umbrella 31 is collapsible.

Viewing FIGS. 4g and 4h, when barbs 40 are collapsible (generally, foldable inward toward anchor shaft 120), a barb retaining device 94, such as a ring 95 (see FIG. 4g), or a sleeve 96 (see FIG. 4h and FIG. 15), may slide over shaft 120 to collapse barbs 40. Retaining device 94 is retractable down shaft 120, and may be placed over a collapsed barb 40 to hold barb 40 in a collapsed position. When barb end 21 is inserted into tissue, barb-retaining device 94 move down shaft 120 as barb 40 slides through barb-retaining device 94 and deploys into the tissue. Barb 40 stays collapsed, however, as long as the barb sidewalls contact tissue. After penetration of tissue, barb 40 expands, and resists removal from the tissue. Barb 40 also creates resistance by the counter-traction that occurs when barb 40 is imbedded within the tissue.

Materials of construction for anchor 20 are preferably biologically-inert plastics, thin stainless steel, or other non-reactive materials that can co-exist within a tissue with little or no adverse patient reaction. Portions of anchors 20, however, should be sufficiently rigid to insure that anchor 20 cleanly and precisely penetrates the tissue at the desired location and that a deployed barb 40 will resist removal from tissue. Generally, the portion of shaft 120 attached to plunger 5 or attached to anchor stay 50 should be fairly rigid.

Barb end 21 may also be shaped to penetrate a tissue, such as is shown in FIGS. 4a, 4b, 4f, and 4h. When anchor 20 has a barb end 21 that is ill-suited to penetrate a tissue (see FIGS. 4c and 4e), anchor 20 is preferably used with delivery device 1 having hollow barrel portion 7 that is shaped to penetrate a tissue. For example, see sharp end 125a shown in FIG. 7a.

Viewing FIG. 7a, if barb 40 comprises a T-shaped head 33, anchor 20 may be loaded into delivery device 1 using forceps. Shaft 120 is a flexible material that allows placement of T-shaped head 33 as shown. Sharp end 125a of hollow barrel portion 7 is adapted to penetrate a tissue. A portion of shaft 120 extends through slot 9 configured in housing sidewalls 9a. Preferably, barb end 21 has a larger cross-section than shaft 120, and prevents removal of barb end 21 through slot 9. Plunger 5 engages anchor 20. Though not shown, anchor end 10 of plunger 5 may comprise a clip member 12 designed to partially encircle shaft 120 (see FIG. 1a for example).

Viewing FIG. 7b, anchor end 10 of plunger 5 may comprise circular-shaped disk 43 with a slot 41 into which shaft 120 is slidably inserted. Shaft 120 passes adjacent to plunger 5 and exits the bottom of delivery device 1, eliminating the need for slot 9. Alternatively, but not shown, anchor end 10 may have slot 41 that works in conjunction with slot 9 located on sidewalls 9a. In such an embodiment, slot 41 aligns with slot 9, enabling shaft 120 to exit hollow barrel portion 7 below anchor end 10.

Figure 9A:
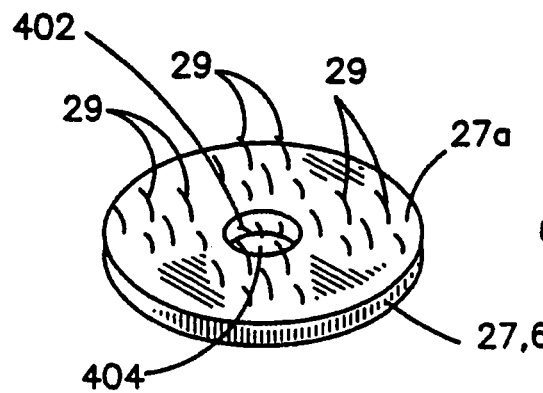
FIG. 9a illustrates an embodiment of a tissue-anchor retaining device shown as a disk.
Figure 9B:
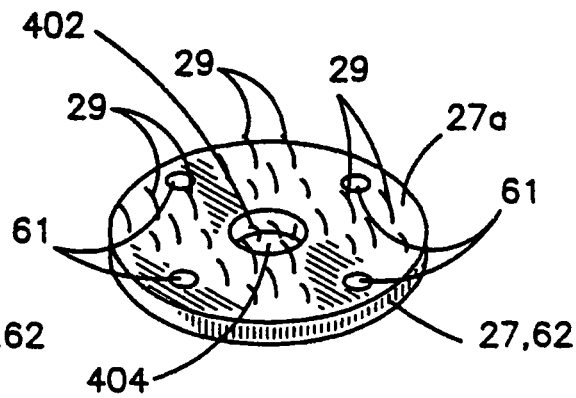
FIG. 9b illustrates another embodiment of a tissue-anchor retaining device shown as disk having suture apertures therein.

Viewing FIGS. 6a-6g, attachment member 23 is a structure generally located on shaft 120 for engaging a material, such as a suture or tissue sample, a second barb end, or a tissue-retaining device 27 (shown in FIGS. 9a and 9b). Tissue-retaining device 27 may comprise a disk-like washer or button 62 (see FIGS. 9a and 9b) or simply a lip that operates in conjunction with attachment member 23 and reversibly mates with attachment member 23. Viewing FIGS. 6a-g, attachment member 23 comprises one or more openings 50a in shaft 120 (or a tabbed portion 23c thereof) (see FIGS. 6a and 6b); a ring 51 (see FIG. 6c), a tissue clamp 52 (see FIG. 6d), ratcheting devices, such as series of projection fingers 55 (see FIG. 6e) or annular projections 56 (see FIG. 6f) extending radially from shaft 120, or a series of indentations 58 in shaft 120 (see FIG. 6g), all of which comprise interleaving members.

Alternatively, viewing FIG. 6e, attachment member 23 may comprise a combination of the above, such as openings 50 and fingers 55. Viewing FIG. 6d, clamp 52 has first and second reversibly interlocking surfaces 53, 54 that may clamp onto tissue. As shown in FIGS. 6e and 6f, fingers 55 or projections 56 may attach a tissue-retaining device 27 (not shown, see FIG. 16f) onto shaft 120, thereby allowing retaining device 27 to compress and retain a tissue between barb end 21 (or tip 130) of the anchor shaft 120 and retaining device 27. This embodiment is well-adapted to support organs whose connective supportive tissues have weakened or failed, such as the transvaginal sacral or sacrospinous colpopexy later described.

Viewing FIGS. 9a and 9b, tissue-retaining device 27 is an annular disk-like structure, sometimes referred to herein as a "porcupine" button 62. Button 62 has a center hole 404 sized for positioning around shaft 120 and attachment member 23. The top surface 27a of button 62 may be arcuate-shaped, and have a series of projections 29 extending outwardly from top surface 27a. Projections 29 grasp tissue to prevent button 62 from migrating. Viewing FIG. 9b, to resist migration of button 62 relative to tissue, button 62 may have a series of holes 61 extending therethrough around the periphery for suturing button 62 to tissue. Alternatively, button 62 may be constructed of a mesh material, allowing sutures to extend therethrough. A surgeon must ensure contact between button 62 and shaft 120 does not interrupt blood supply to that area in contact with tissue-retaining device 27.

If attachment member 23 is as a ratcheting device, such as fingers 55 projecting from the exterior sidewalls of shaft 120 as shown in FIG. 6e, or a series of indentations 58 (see FIG. 6g), and tissue-retaining device 27 is button 62, button 62 may slide up or down shaft 120. However, button 62 is retained in a given position on shaft 120 by the inter-mating of the ratcheting devices on shaft 120 and within button center hole 404. Center hole 404 may have a series of fingers 402, or other projections, extending outwardly to interact with the interleaving members or ratcheting devices on shaft 120 to accomplish the same function. Generally, button 62 has a first interleaving member (fingers 402) on the interior walls of hole 404, while anchor 20 will have a second interleaving member (such as projections 701 in FIG. 8c) positioned thereon. The first and second interleaving members cooperate to resist movement of button 62 relative to anchor 20. Alternatively, a C-clip or other clip member 12 on delivery device 1 may be used as a retaining device 27 to keep anchor 20 properly positioned relative to the tissue.

Viewing FIGS. 4a, 4c, and 4e, if sutures are placed through attachment member 23, they are preferably installed when anchor 20 is loaded into delivery device 1 so that: (a) the surgeon does not have to position sutures through openings 50a after anchor 20 is attached, and (b) if the sutures are sufficiently long to reach back to the surgeon during placement of anchor 20, the surgeon will not fish for the sutures in the body cavity. To assist a surgeon in tailoring anchor 20 to a particular application, attachment member 23 may be detachable from anchor 20 (e.g., threaded onto shaft 120, or clipped onto shaft 120 or the base of barb end 21, etc). Shaft 120 has a small cross section at tip 130, much like a needle tip, such as 1-3 mm, to allow easy penetration into tissue.

Viewing FIG. 19a, anchor 20 and attachment member 23 may comprise separate elements. Anchor 20 has a barb 102 positioned on a shaft 120. Attachment member 23 comprises a housing 1000, and shaft 120 is movably inserted through housing 1000. Housing 1000 comprises an upper portion 1005 and a lower portion 1006 rotatably engaged using interlocking lips 1007, 1007a. Interlocking lips 1007, 1007a are slidably engaged, and to assist rotation, a bearing 1009 or other suitable device may be included. Shaft 120 is movably positioned within housing 1000 via corresponding threads 1004, 1004a.

An alternate embodiment is shown in FIG. 19b. Housing 1000 and shaft 120 engage each other with interleaving members, or ratcheting devices 140, 150, such as grooves 1001 in housing 1000 and corresponding projections 1001a positioned on shaft 120. Interleaving members 1001, 1001a allow the position of shaft 120 to be fixed relative to housing 1000. Shown on shaft 120 is an attachment member 23 and holes 50a for attaching sutures or other suitable items.

The embodiment shown in FIGS. 19a and 19b, allows a surgeon to adjust the position of shaft 120 relative to attachment member 23 and items attached to attachment member 23 during placement of the tissue-anchoring system. The embodiment in FIG. 19b can be adjusted using an adjuster cylinder 90, and the embodiment in FIG. 19a can be adjusted by rotating shaft 120, causing shaft 120 to move up or down.

Examples of Use of the Anchoring System

Viewing FIG. 7a, to set anchor 20 in tissue, a surgeon positions a loaded delivery device 1 against the tissue to be penetrated for insertion of anchor 20. If the delivery device 1 has a hollow barrel portion 7 designed to penetrate tissue, then hollow barrel portion 7 is placed against the tissue, and delivery device 1 is advanced with hollow barrel portion 7 penetrating tissue. When hollow barrel portion 7 has advanced so that sharp end 125a clears the tissue or is embedded therein, plunger 5 is advanced, releasing anchor 20. Hollow barrel portion 7 is withdrawn from the tissue, leaving anchor 20 supported within the tissue or by a tissue surface 601 (not shown). If delivery device 1 has a hollow barrel portion 7 that will not penetrate tissue, then anchor 20 should be equipped with a sharp end 125 (not shown, see FIG. 8a) designed to penetrate a tissue. In this embodiment, hollow barrel portion 7 is placed against the tissue, and plunger 5 advanced, forcing anchor 20 into tissue. When anchor 20 has advanced sufficiently into tissue or through tissue, delivery device 1 is withdrawn, leaving barb 40 embedded into tissue, or inserted through tissue.

Viewing FIGS. 11a-11c, if delivery device 1 has no hollow barrel portion 7, (for example, the anchoring system as shown in FIG. 1a) then barb 102 of anchor 20 is adapted to penetrate a tissue. In such an embodiment, anchor 20 is placed against the tissue to be penetrated, the delivery device 1 advanced (or if it is plunger-equipped, plunger 5 is advanced), until anchor 20 has advanced sufficiently into tissue or through tissue, at which time the delivery device 1 is withdrawn.

Figure 20:
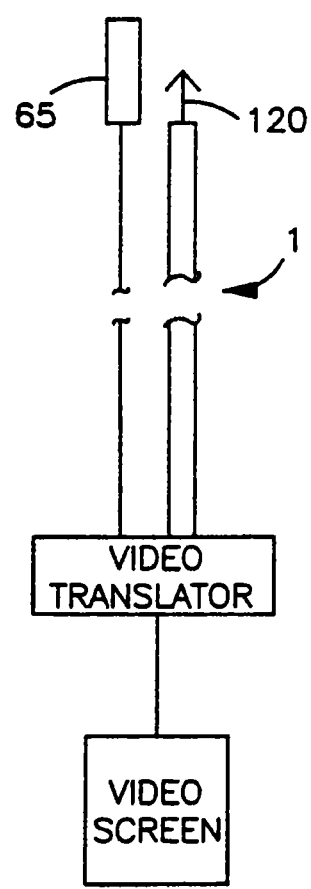
FIG. 20 illustrates a schematic view of an anchor deployed within a flexible delivery device that also incorporates a micro-video camera and video screen.

This anchoring system may also be used in less surgically technical operations for surgeons who are not comfortable with transvaginal approaches in laproscopically-assisted sacral colpopexy operations. The surgeon may place anchor 20 into the anterior longitudinal ligament of the sacrum laproscopically or endoscopically and secure the vaginal vault to the sacrum transvaginally in a laproscopically assisted sacral colpopexy. Alternatively, the system may be used with a microscopic video camera 65 located near tip 8 of delivery device 1 as seen in FIG. 20. The anchoring system would be placed into and or through the apex of the vaginal vault using a rigid or flexible delivery device 1, either endoscopically or transvaginally, to fix anchor 20 to suspend the vault to the sacrum. The anchoring system can also be used endoscopically with an operative single port laparoscope thereby obviating the need for multiple puncture sites in the abdomen when performing this procedure. The anchoring system obviates the need for other bulkier surgical instruments currently used for retropubic bladder neck suspension, retropubic Goebell-Stoeckel sling procedures, and multiple abdominal scope port sites. This anchoring system also obviates the need for using bone anchors and obviates the associated well-known complications. In addition, by using the tissue anchoring system and an intervening connector to attach to a sling of harvested tissue, the size of the material harvested or used in the sling can be decreased in size, thereby minimizing the amount of graft tissue or donor tissue needed to be used. In turn, this minimizes the amount of graft tissue and operative harvesting technique, thereby minimizing complications, such as hematoma formation, pain, infection and decreased strength of the upper leg. In addition, the retropubic Goebell-Stoeckel sling could be used using a smaller fascia sling graft or donor graft using an umbrella shaped anchor head 31 with an extended anchor shaft 120 armed at both ends creating a u-shaped anchor that seats into the rectus fascia 603 via an exclusively transvaginal approach.

As indicated, the system can be used with a tissue clamp 52 as attachment member 23 (see FIG. 6d). Clamps 52 fix the ends of a fascia sling for the Goebell-Stoeckel fascia sling procedure and obviate the need for sutures. A general outline of the transvaginal-endoscopic-sacralcolpolexy procedure using an endoscope-adapted tissue anchor system follows. The patient is placed into the dorsal lithotomy position and undergoes general or spinal anesthesia. The vaginal cuff is visualized using angled surgical retractors. A transverse incision is made just inside the hymenal ring on the posterior wall and extended down the mid-line of the posterior vaginal wall, sharply and bluntly dissecting the vaginal mucosa from the underlying supportive tissue of the vagina to the apex of the vault. The retroperitoneal space would be accessed using sharp and blunt dissection revealing the sacral promontory to the S2 and S3 areas of the sacrum and the anterior longitudinal spinal ligament.

The vaginal cone speculum is inserted up to the anterior longitudinal spinal ligament. The middle sacral vessels are visualized and isolated to the exterior of the cone using blunt retraction. If this is impossible and there is a significant risk for damage to these vessels, the vessels may be ligated using a hemoclip-extended applicator transvaginally through the vaginal cone superior and inferior to the operative sites. If bleeders are encountered in the retroperitoneal space while dissecting the anterior longitudinal spinal ligament, they could be fuilgurated using a Klepinger electrocautery device or hemoclip. The surgeon secures the tip and rim of the vaginal cone against the sacrum maintaining isolation of the operative site while inserting a flexible fiberoptic endoscope into the vaginal cone at the sacrum loaded with the flexible tissue-anchor applicator. The tissue anchor 20 is loaded onto a delivery device 1. The shaft of the anchor is advanced into and parallel to the under surface of the anterior longitudinal spinal ligament for approximately one centimeter. The appropriate angle of insertion is facilitated by the manipulation of the flexible tip of the anchor/anchor applicator and/or endoscope by the surgeon at the operator end of the endoscope. The delivery device 1 is advanced through the operative port of the endoscope thereby advancing the anchor with barb end through the anterior longitudinal spinal ligament to the desired depth. Plunger 5 is depressed and advances anchor 20 into the space anterior to the sacrum but just beneath the anterior longitudinal spinal ligament. Delivery device 1 is withdrawn into the endoscope.

The surgeon visualizes anchor 20 in the anterior longitudinal spinal ligament. The endoscope is withdrawn trailing the sutures which are attached to anchor 20 back into the vaginal cone speculum and towards the surgeon at which time they are grasped in a clamp for later attachment to a synthetic mesh, fascia lata or rectus fascia 603 graft for later suspension of the vaginal vault to the sacrum. If necessary, several anchors 20 may be placed into the anterior longitudinal spinal ligaments in this fashion.

An extended suction device is used to enhance visualization of the space at the operative site. A suction irrigator device is preferred. The synthetic graft is attached to the trailing sutures from the anchor(s) 20 and then advanced up the vaginal cone speculum, applied to the sacrum and tied in a fashion similar to that done during an endoscopic procedure with an extended knot pusher. This secures the proximal portion of the graft at the anterior longitudinal spinal ligament. The distal portion of the graft is secured to the vaginal vault apex using: (a) the standard transvaginal surgical instruments that one would use during a vaginal hysterectomy, or (b) the adjustable tissue anchor clasp and adjustable suture connector for attachment and adjustment of the vaginal cuff. The graft application is performed entirely in the retroperitoneal space. Before placing the sutures at the vaginal vault apex, the surgeon ensures that the sutures are placed into the graft at a site that allows appropriate length between the vaginal apex and the sacrum minimizing any excessive tension on the mesh or fascial graft. The vaginal cuff is then closed in a manner used in the standard posterior-colporhaphy procedure, well-described in the gynecologic surgical literature. Because this procedure is carried out endoscopically (or manually) in the retroperitoneal space, there is no need for abdominal entrance and/or closure of the parietal peritoneum over the mesh or fascial graft. This ensures that there are no internal hernias postoperatively, and the operation is totally extra-peritoneal thereby minimizing ileus. The surgeon should be careful and concerned about hemostasis and ensuring that the colon and ureter are not damaged during the procedure. The vaginal cone at its apex should be padded with a soft silicone gasket to ensure that tissues are not unduly traumatized.

Tissue anchor 20 can also be used in the post-operatively adjustable transvaginal-sacrospinous-colpopexy procedure as follows. The patient is placed in a dorsal lithotomy position after undergoing general or spinal anesthesia. This procedure may be performed using local anesthesia for patients who have medical conditions that may be complicated by either spinal or general anesthesia. A weighted speculum is placed in the posterior vault. A Sics retractor is placed anteriorly. The cuff apex is visualized if the uterus and cervix have been removed. In the lateral vaginal fornices, a 0.5-1.0 centimeter (cm) vaginal mucosa incision is made, and a 1-2 cm.sup.2 area of vaginal mucosa undermined at these sites. This reveals the underlying submucosal vaginal-supportive tissue. Tissue-anchor delivery device 1 is placed into the surgeon's hand and advanced into the vagina. The tissue-anchor delivery device 1 with a loaded tissue anchor 20 is advanced up the vagina and punctures the vaginal tissue through the lateral fornices of the vagina on the patient's right side directly through the area which was previously undermined. Tissue-anchor delivery device 1 places anchor 20 into the sacrospinous ligament as follows. The sacrospinous ligament is located after the surgeon palpates the ischial spine, and anchor 20 is placed approximately 2 cm medial to the ischial spine through the sacrospinous ligament mid-portion. Tissue-anchor 20 deploys into and/or through the sacrospinous ligament, and delivery device 1 is withdrawn from the vagina leaving anchor 20 in position transfixing the vagina vault apex to the sacrospinous ligament. The chosen anchor 20 depends on the surgeon's desires.

Anchor 20 may be adjustable or non-adjustable. Viewing the embodiments shown in FIGS. 16*a*-16*h* or FIG. 17, adjustable tissue anchors 20 are used as follows. Anchor 20 is positioned as previously described, transfixing the lateral vaginal cuff apex to the sacrospinous ligament. Delivery device 1 is then removed. This leaves the adjustable shaft 120 in anchor 20 trailing from the lateral vaginal apex into the vaginal canal. A 1-1.5 cm.sup.2 "porcupine" button 62 is then advanced onto shaft 120 and ratcheted into place using the interleaving members 303, 304 or ratcheting devices 140, 150 positioned on shaft 120 and in some instances using the interleaving members (fingers 402) positioned in center hole 404, thereby opposing the lateral vaginal cuff apex to the sacrospinous ligament. The vaginal cuff apex may be clasped or sutured alternatively to anchor 20. The same procedure is carried out on the opposite side. This suspends the vaginal cuff apex to the sacrospinous ligament either unilaterally or bilaterally. The trailing end of shaft 120 may be used for adjusting the vaginal cuff tension postoperatively and then trimmed flush with anchor body 99 when the appropriate tension is achieved. If the surgeon does not want a foreign body in the vagina, a standard adjustable tissue anchor 20 could be used, the vaginal cuff apex sutured to anchor 20, and vaginal suspension tension adjusted postoperatively to ensure patient comfort.

The vaginal mucosa is closed using either running- or interrupted-absorbable sutures over button 62 at the lateral vaginal cuff apices. In addition, button 62 may be sutured to the submucosal vaginal tissue along its circular perimeter before closure of the vaginal mucosa to ensure its appropriate fixation in the tissues. The lateral circular rim of button 62 may be composed of a mesh-like synthetic material, to facilitate penetration of fibroblasts and granulation tissue to ensure fixation of the button in the subvaginal mucosal tissue.

The procedure is preceded by the appropriate preparation of the surgical site with an antiseptic solution such as iodine or other antiseptic and appropriate draping to ensure sterile technique. The patient should also receive pre-operative prophylactic antibiotics, approximately one to two doses, and one to two doses postoperatively after closure of the vaginal mucosa to prevent postoperative infection from a foreign body.

This procedure obviates the need for extensive vaginal dissection as described in other techniques used in vaginal vault suspension such as sacrospinous ligament fixation using the tendon sheath punch, or the hook-like suture carriers. Other vaginal vault suspension procedures require a more extensive dissection of the posterior vaginal vault and submucosal tissue. This more extensive dissection can result in serious hemorrhage. The procedure is done with a minimal amount of vaginal dissection—approximately 4 cm.sup.2 divided at two locations.

There is also minimal manipulation of the sacrospinous ligaments and surrounding tissue. This procedure requires only a single puncture of the sacrospinous ligament. The operative time would be substantially decreased as a result of the simplicity of operative dissection insertion of the tissue anchor system and the ability to adjust vaginal suspension tension postoperatively, as later described. This procedure could be used on an outpatient basis.

Adjustable Tissue Anchor

An embodiment of an adjustable anchoring system is shown in FIGS. 8*a*-8*c*. FIG. 8*a* illustrates an anchor 20 comprising a body 99 having a hollow chamber 100 therein and a shaft 120 insertable within body 99. Shaft 120 is sized to be at least partially insertable into hollow chamber 100 and moveable relative to hollow chamber 100. Hollow chamber 100 may pass completely or partially through body 99. Viewing FIG. 8*b*, if hollow chamber 100 extends partially through body 99, body 99 preferably has a slot 89 that allows shaft 120 to exit hollow chamber 100 through sidewall 89*a*. Shaft 120 has a tip 130 adapted to penetrate a tissue. Tip 130 should be fairly rigid to ease tissue penetration, although a flexible tip 130 is preferred for certain procedures, such as transvaginal sacral colpopexy. Viewing FIGS. 16*a*-16*g* and FIG. 18*b*, shaft 120 may have indicia markings 80 thereon (e.g. millimeter (mm) markings or color change markings) as indicators that allow a surgeon to determine the extent of tension adjustments. Shaft 120 may have a cross-section that is round, flat, rectangular, or any other suitable shape.

The end of shaft 120 opposite tip 130 has an attachment member 23 attached thereto or constructed as part thereof. Hollow chamber 100 has a barb end 101 with at least one barb 102 positioned thereon. Barb 102 resists removal of anchor 20 from a tissue after anchor 20 has been inserted into or through tissue. Barb end 101 may be a variety of shapes but is easily insertable into tissue, generally having a sharp end 125 and a collapsible barb 102 for use in conjunction with a barb retainer 94, as previously described.

Viewing FIG. 8c, body 99 may also have a ratcheting device 701 positioned on body outer walls 703 distal from barb end 101. Ratcheting devices 701 may comprise a series of fingers, annular projections 702, indentations, or threads to adjustably and matingly engage tissue-retaining device 27, such as button 62. Alternatively, tissue-retaining device 27 may comprise a washer-like structure that snaps or clips onto shaft 120 where desired. Though not shown, body 99 may also have a stop 70 projecting away from body walls on the end distal from barb end 101 to prevent the body 99 from inserting completely through the desired anchoring tissue.

Figure 5B:
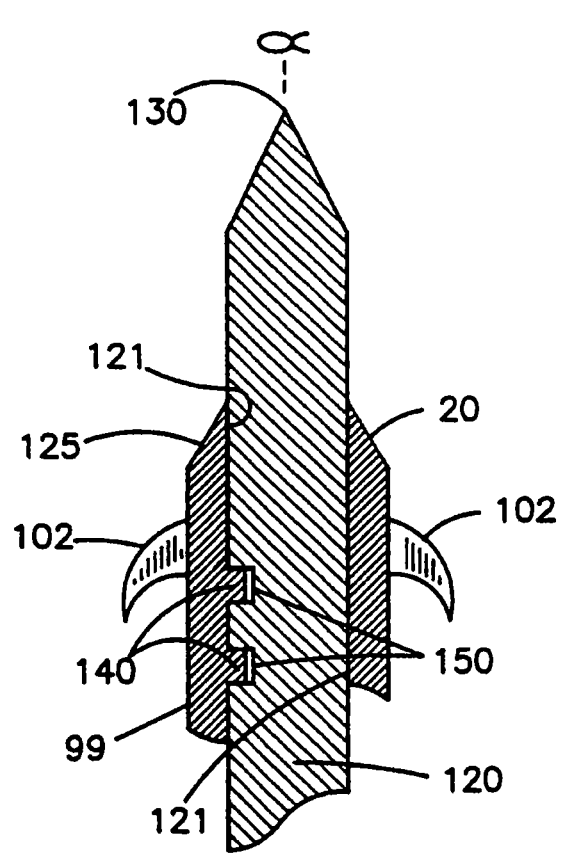
FIG. 5b illustrates an embodiment of an anchor having a shaft positioned therein, wherein ratcheting devices are positioned on only one side of the anchor and a corresponding side of the shaft.
Figure 5C:
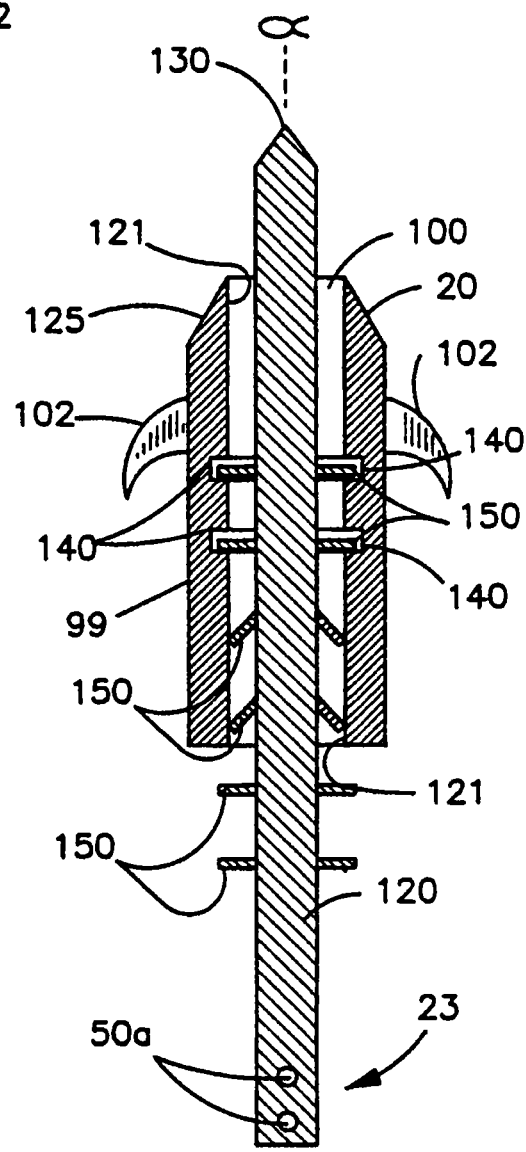
FIG. 5c illustrates the embodiment of the anchor shown in FIG. 5a shown with a shaft inserted therethrough, illustrating first and second ratcheting devices engaged.
Figure 10A:
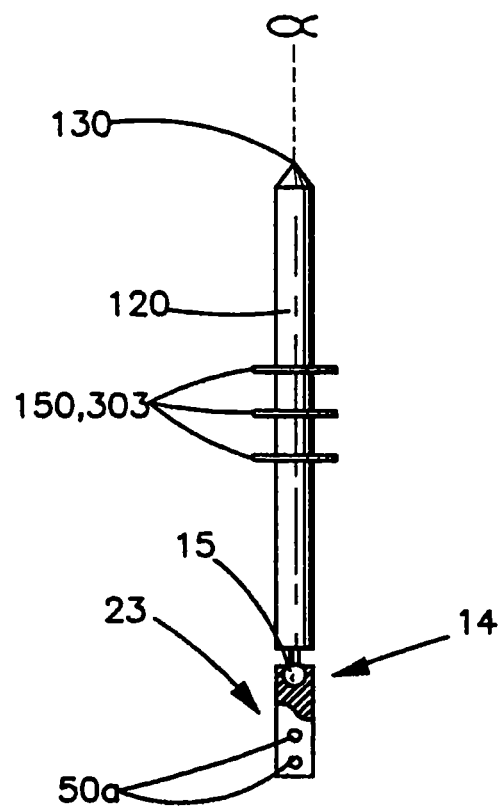
FIG. 10a illustrates an embodiment of a shaft having annular projections as ratcheting devices wherein the attachment member is rotatably attached.
Figure 10B:
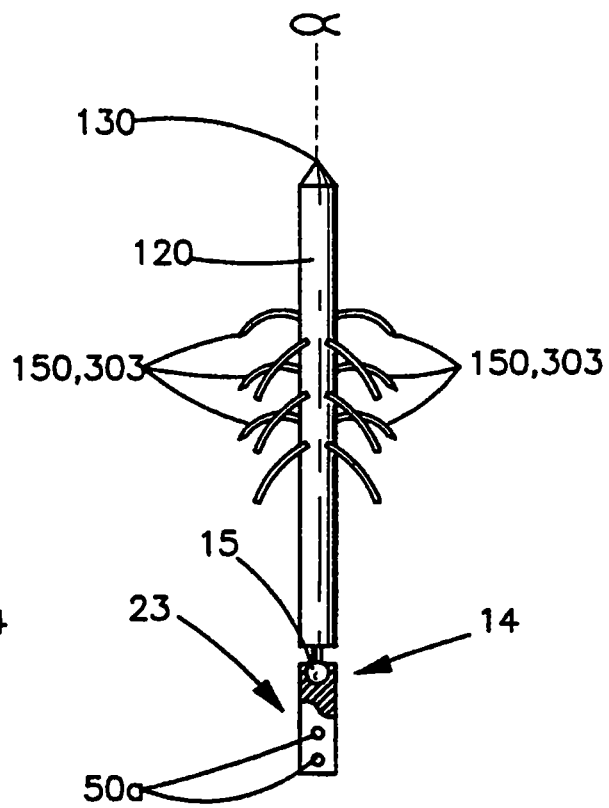
FIG. 10b illustrates an embodiment of a shaft similar to the embodiment shown in FIG. 10a wherein the ratcheting devices are finger-like projections.

Viewing FIGS. 5a-5c, the interior walls 121 of hollow chamber 100 may have a first ratcheting device 140. First ratcheting device 140 may be a series of annular ridges, threads, projections, indentations or other shapes designed to interlock or interleave with a second ratcheting device 150 located on exterior of shaft 120 (such as interlocking male and female threads, indentations and corresponding projections (see FIG. 5b), interleaving sidewall fingers 303 shown in FIGS. 16a-16h, interleaving annular projections 1001a shown in FIG. 19b, and FIG. 5c). Variation in the number or type of interleaving members or ratcheting devices or their materials of construction will vary the load-support capability of a particular anchor 20. Ratcheting devices 140, 150 create a two-way ratcheting-type mechanism that positions shaft 120 relative to body 99. Shaft 120 may be adjusted in steps by pulling or pushing shaft 120 relative to body 99 (or turning, in the case of interlocking threads). If ratcheting devices 140, 150 comprise male and female threads, it is desirable that shaft 120 have a ball bearing 15 or other pivotally rotatable mechanism 14 located in attachment member 23 as shown in FIGS. 10a and 10b.

Mechanism 14 allows shaft 120 to turn independently of the bottom of shaft 120 where attachment member 23 is located. Mechanism 14 prevents twisting of sutures, slings, or other devices attached to attachment member 23. This twisting may occur during later tension adjustments, either intra- or post-operative.

Anchor 20 is set by first setting outer hollow chamber 100 and then shaft 120 with the surgeon's hand or with a delivery device 1. A delivery device 1 is preferred because anchor 20 may be relatively small. Viewing FIG. 12, delivery device 1 may comprise a housing 2 and finger grips 3, but other previously-described embodiments may also work.

Alternatively, anchor delivery device 1 may include a hollow barrel portion 7 wherein at least a portion of shaft 120 is positionable therein. Hollow barrel portion 7 has a lip section or edge 300, sized to fit within hollow chamber 100. Though not shown, a stop member may be positioned on body 99 to prevent body 99 from being deployed completely through tissue. Though not shown, delivery device 1 may optionally include a plunger 5 slidably positioned in hollow barrel portion 7. Inclusion of a plunger 5 in the embodiment of FIG. 12 requires that plunger 5 adapt to allow shaft 120 to pass through or by plunger 5 (e.g., plunger 5 as shown in FIG. 7b). In such an embodiment, plunger 5 alone activates shaft 120.

Figure 13:
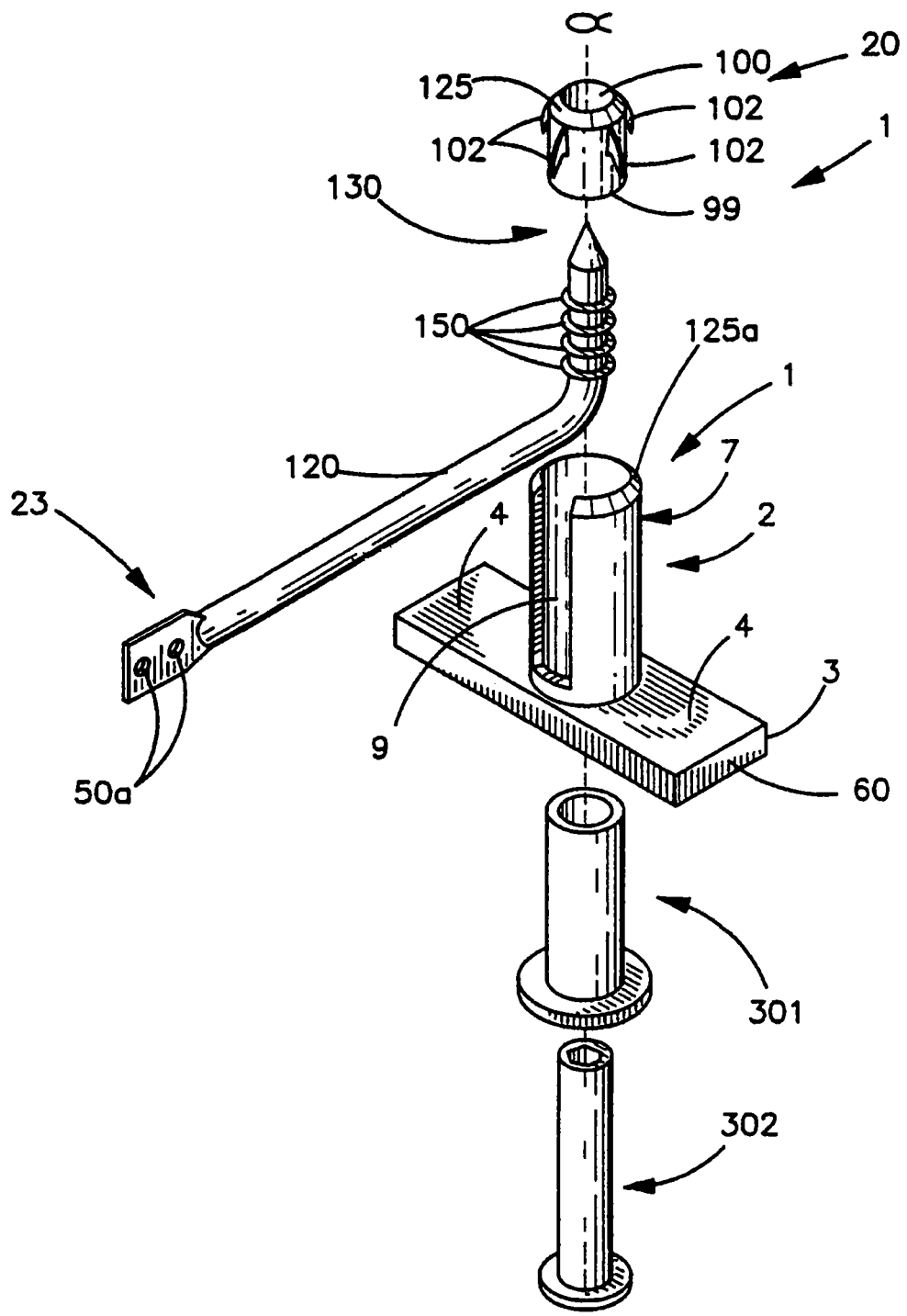
FIG. 13 illustrates an embodiment of a delivery device comprising two plungers.

Alternatively, as shown in FIG. 13, housing 2 may have a hollow barrel portion 7 that is adapted to have anchor 120 positioned at least partially therein. Hollow barrel portion 7 should have a sharp end 125a adapted to penetrate a tissue. This embodiment is appropriate when barbs 102 are ill-suited to penetrate a tissue. Delivery device 1 may further comprise one, two or no plungers. In a two-plunger embodiment, a first plunger 301 activates body 99 after hollow barrel portion 7 has penetrated a tissue, and second plunger 302 activates shaft 120 after barbs 102 deploy. FIG. 13 illustrates a two-plunger embodiment comprising concentric first and second plungers 301, 302. A single-plunger embodiment may be used if either plunger 301 or 302 activates either body 99 or shaft 120. However, if a single plunger is adapted to activate shaft 120, the surgeon should rely on the friction between first and second ratcheting devices 140, 150 on body 99 and shaft 120 to cause deployment of body 99 when the plunger is depressed. After barbs 102 deploy, shaft 120 may be accessed through the skin surface 601 (see FIG. 16f) by a surface incision as will be later described. Though not shown, housing 2 may also have a projecting ridge 60a located on the external side of hollow barrel portion 7 to act as a stop 60.

Figure 14:
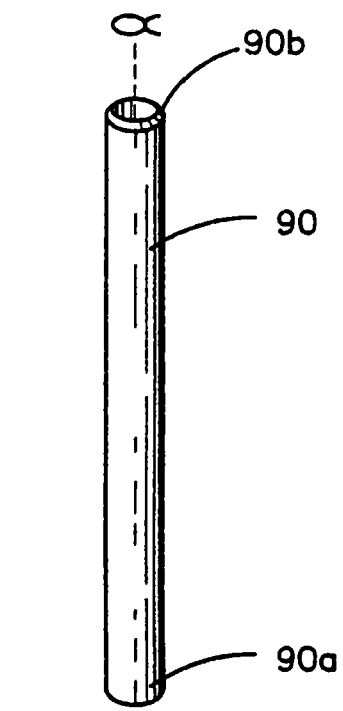
FIG. 14 illustrates an embodiment of an adjuster cylinder.
Figure 15:
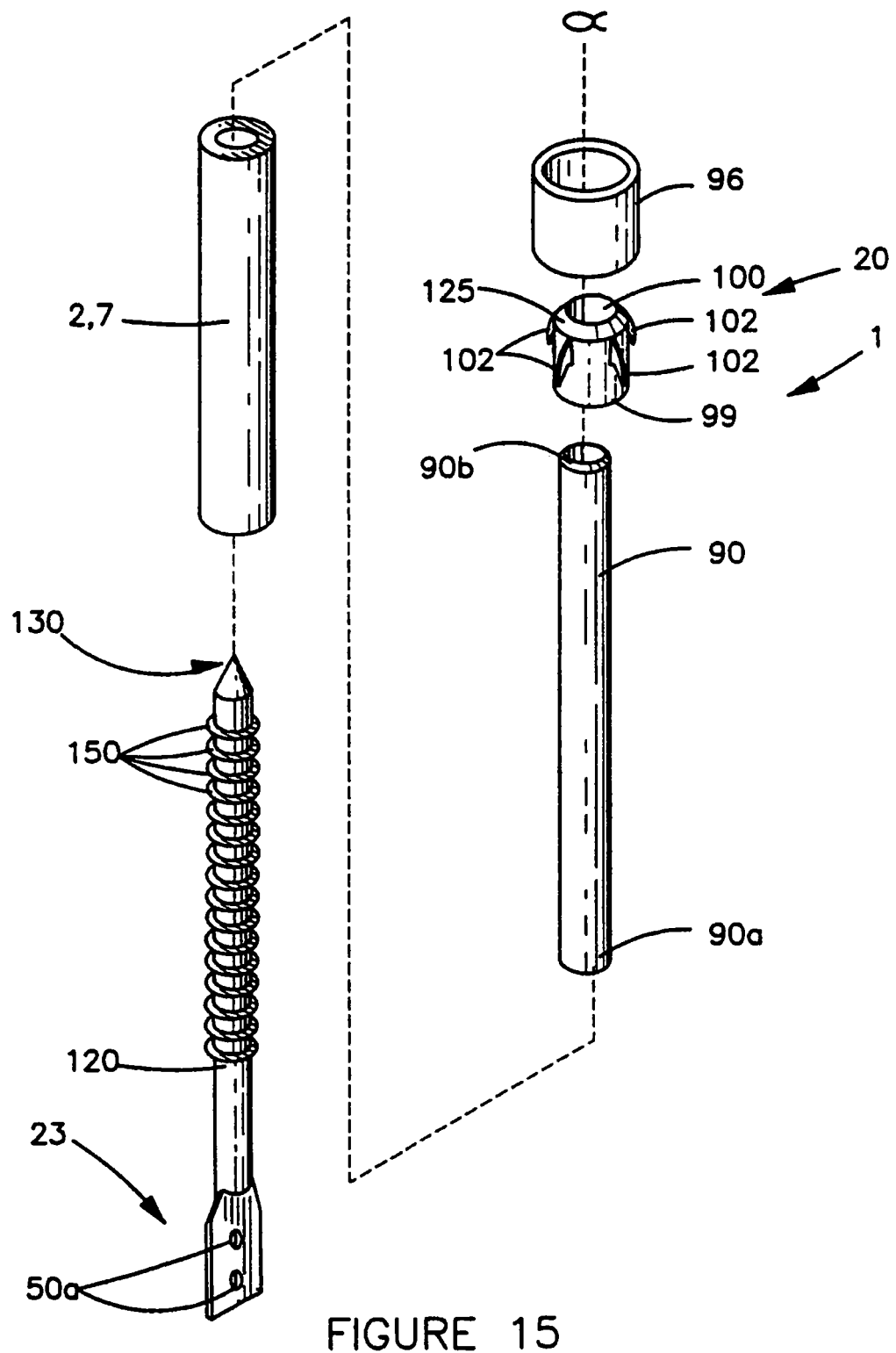
FIG. 15 illustrates an exploded view of an embodiment of the invention incorporating an adjuster cylinder.

Shaft 120 is adjustable upwardly or downwardly, with or without the aid of adjuster cylinder 90 shown in FIG. 14. As used herein, upward and downward shall indicate movement substantially along the central axis of an anchor 20 or housing 2 as shown in the FIGS. FIG. 15 illustrates an exploded view of the invention that shows how adjuster cylinder 90 inserts into hollow chamber 100. Viewing FIG. 15, adjuster cylinder 90 is a hollow tube having an inner and outer diameters sized so that the adjuster cylinder 90 may slide over shaft 120 but slide inside of hollow chamber 100, thereby disengaging the interleaving members 303, 304 or ratcheting devices 140, 150. Adjuster cylinder 90 has a lower end 90a, and may have a cutting edge 90b.

Alternatively, the tissue-retaining device may be as shown in FIGS. 18a-18d. Viewing FIG. 18a, pelvis 600 is shown from a retropubic view. Cooper's ligament 602 is located on pelvis 600. Sutured to Cooper's ligament 602 is anchor 20, which has a hollow portion 66 extending therethrough. Shaft 120 inserts through anchor 20 and is shown exiting skin surface 601. Anchor 20 may be configured with one or more suture holes 67 that allow anchor 20 to be attached to Cooper's ligament 602. In this embodiment, anchor 20 lacks a barb 102. Shaft 120 inserts through hollow portion 66. Shaft 120 is adjusted using a shaft 120 having threads 68 (see FIG. 18c) corresponding to threads position in the hollow portion 66, or by placing corresponding interleaving members or ratcheting devices 140 within hollow portion 66 and corresponding interleaving members or ratcheting devices 150 on shaft 120. Shaft tip 120b may be sharp so that it can penetrate a tissue and skin surface 601.

Figure 18A:
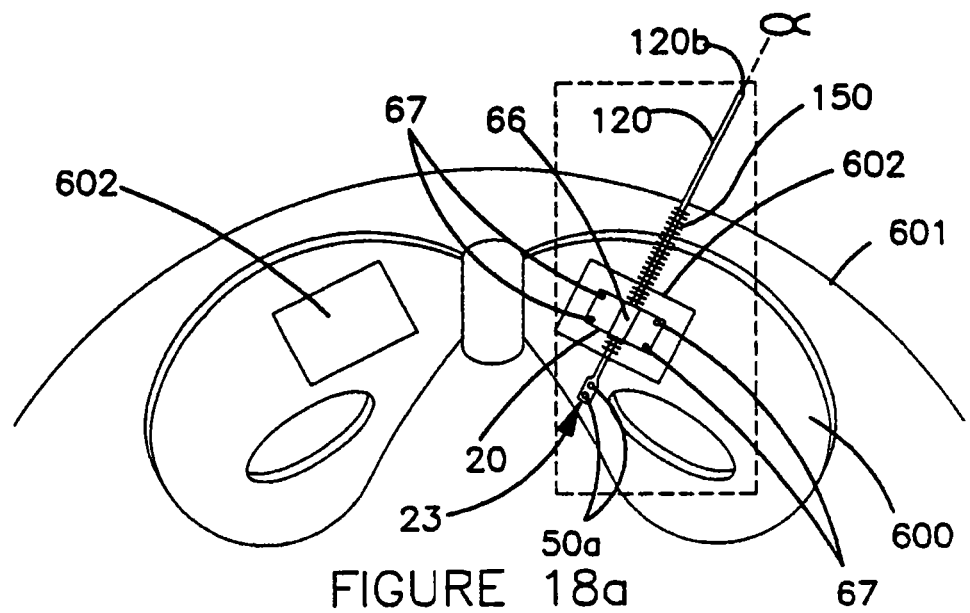
FIG. 18a illustrates an adjustable anchor attached to Cooper's Ligament 602.
Figure 18D:
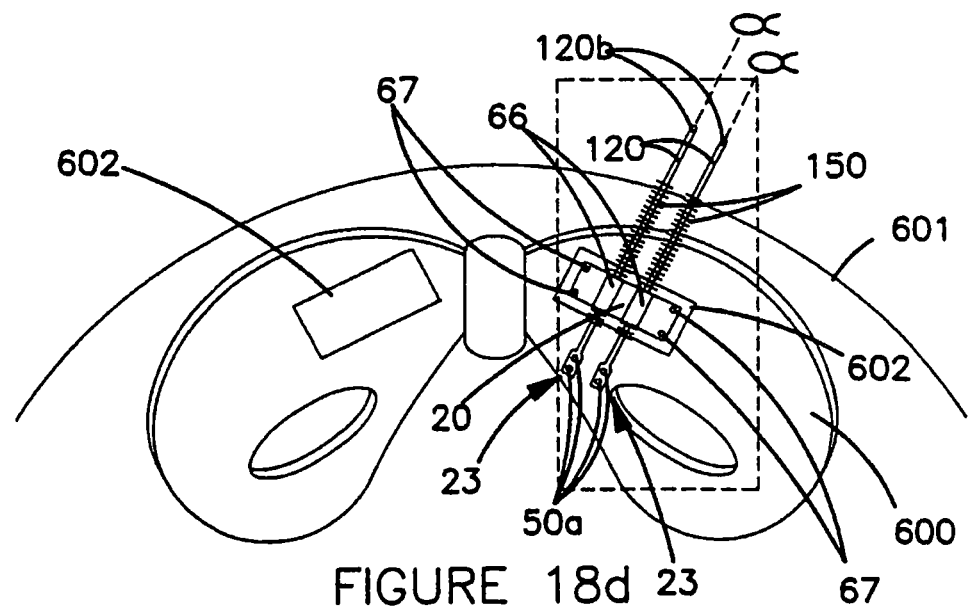
FIG. 18d illustrates an adjustable anchor having a body that accommodates multiple shafts.

Shown in FIG. 18b is an enlarged view of FIG. 18a, to more clearly show ratcheting devices 150 (interleaving members) on shaft 120. Ratcheting devices 150 (interleaving members) shown in FIG. 18b are annular projections similar to those shown in FIGS. 5c and 8a. Shown in FIG. 18c is the same device as shown in FIG. 18b, but shaft 120 has threads 68 positioned thereon allowing shaft 120 to rotatably engage corresponding threads on the interior walls of hollow portion 66. Attachment member 23 rotatably attaches to shaft 120 and is shown as a ball and socket 15. FIG. 18d illustrates an embodiment wherein anchor 20 has multiple hollow portions 66 so that two shafts 120 can engage anchor 20.

Examples of Use of Adjustable Tissue Anchor

Referring to FIGS. 16a-16g, one of the procedures where the adjustable anchor is advantageous is the retropubic bladder neck suspension or retropubic Goebell-Stoeckel sling procedure. In this procedure, it is necessary to support the neck of the bladder through the use of a sling. The following application will demonstrate the use of the adjustable tissue anchor in this procedure, using two anchors: one non-adjustable anchor and one adjustable anchor. If the sling is to be tacked to the bladder neck, it is desirable to use two adjustable anchors. The procedure could be performed transvaginally or by laparotomy.

Figure 12:
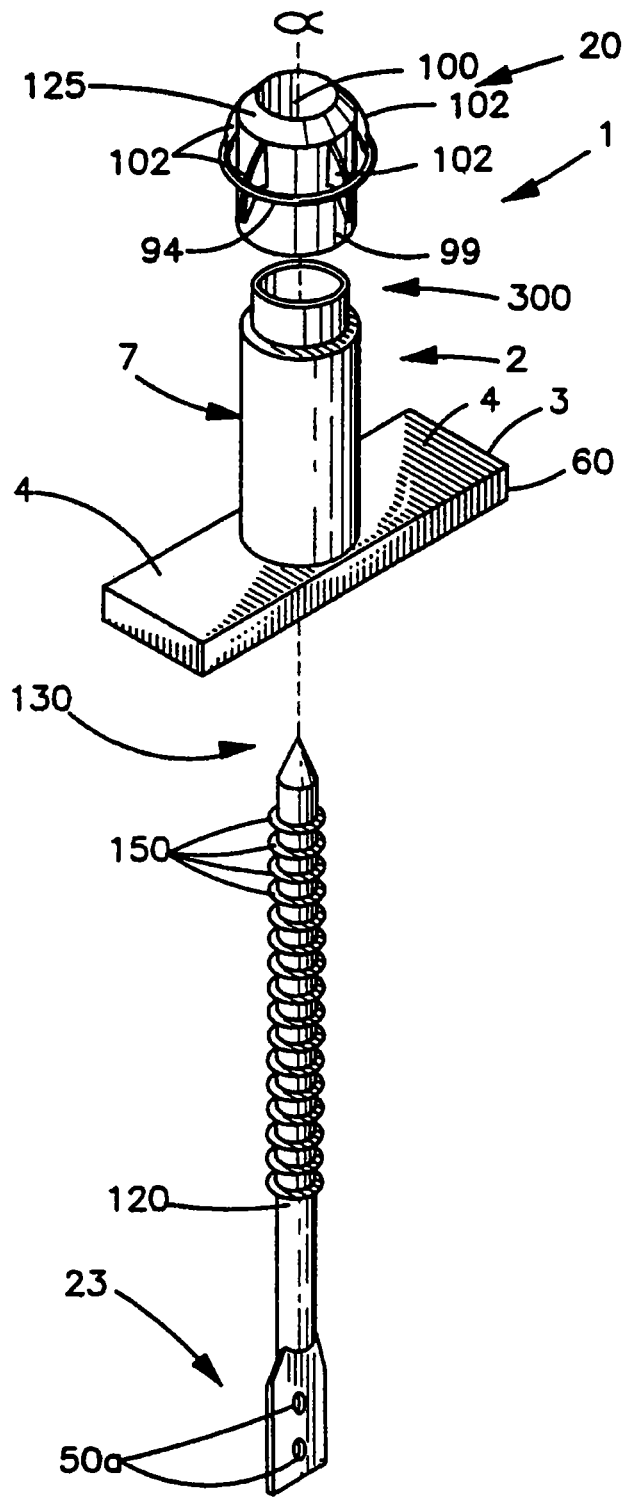
FIG. 12 illustrates an embodiment of a delivery device wherein the anchor slides onto the housing and the shaft slides through the housing and the anchor.

The surgeon first sets a non-adjustable anchor into a suitable connective tissue on one side of the bladder neck, Cooper's Ligament 602 or rectus fascia using the procedure(s) previously described. Anchor 20 may have a sling attached thereto by sutures. The sling is suspended under the urethra and fixed with sutures. The surgeon attaches a second adjustable anchor to the other end of the sling (by use of sutures or by use of a tissue clamp 52 as attachment member 23 on shaft 120) and loads the adjustable anchor 20 onto delivery device 1. Alternatively, the adjustable tissue anchor 20 shown in FIGS. 18a-18c could be sutured to Cooper's Ligament 602, rectus fascia 603, or tendon bilaterally and subsequently adjusted postoperatively. This is accomplished using ratcheting devices 140, 150 ratcheted or thread and screw adjustment mechanism (i.e., interleaving members). The surgeon proceeds to set adjustable anchor 20 into a suitable location on the other side of the bladder neck using a delivery device 1 as shown in FIG. 12 or in FIGS. 5a-5c.

Viewing FIGS. 16a-16g, delivery device 1, with the tissue anchor 20 located therewithin or thereupon, is positioned next to the area where attachment is desired. Delivery device 1 is then advanced forcing shaft tip 130, and the sharp end 125 of body 99 to penetrate into tissue. The barb 102 is retracted or collapsed by barb retainer 94. Retainer 94 remains stationary as the surgeon pushes body 99 into the tissue, and barb 102 moves into or through the tissue via the opening created by body 99. Body 99 and shaft 120 then penetrate and insert through the rectus fascia 603 (tendon or other desired tissue), until barbs 102 are located in the soft subcutaneous tissue between the rectus fascias and the skin surface 601 and deploys. Shaft 120 trails from the tissue into which anchor 20 is embedded. At this point, delivery device 1 may be removed (if desired), and anchor 20 may be anchored at the inferior border of the rectus fascia 603 or underneath the rectus fascia 603 in a sandwich-like fashion by applying a tissue-retaining device 27, such as button 62.

Figure 16A:
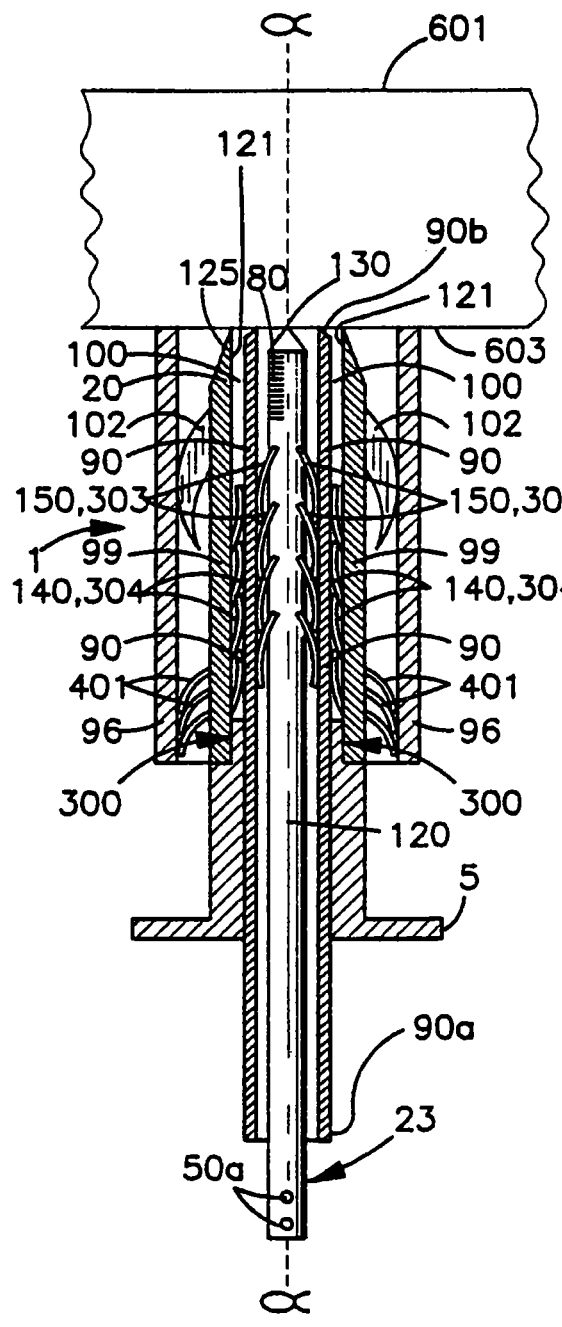
Figure 16B:
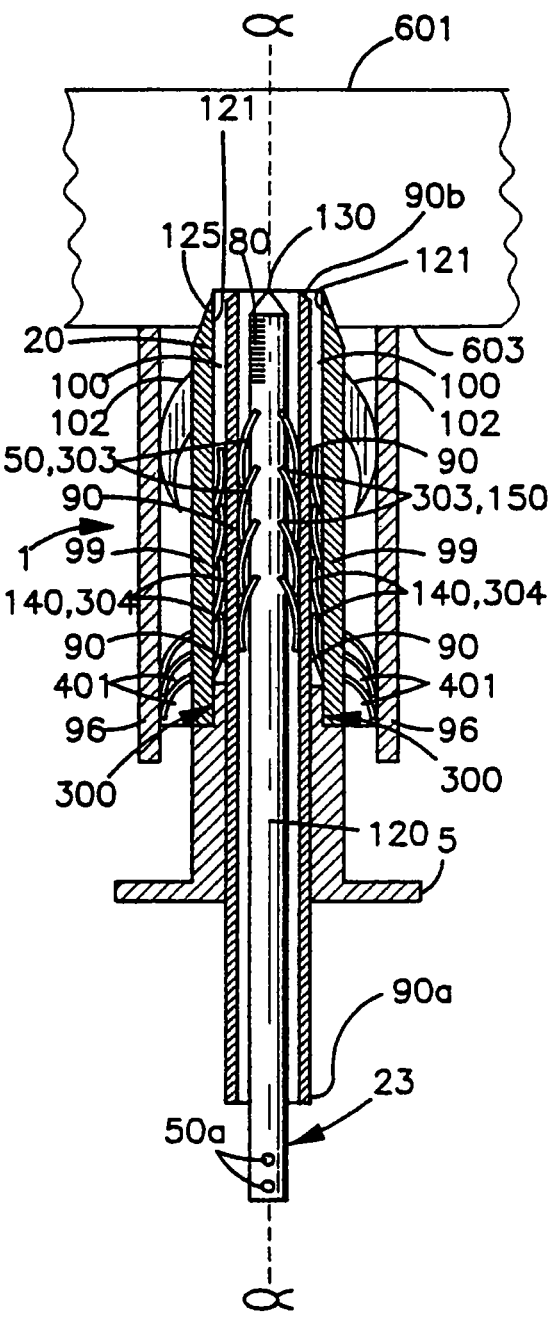
Figures 16C, 16D:
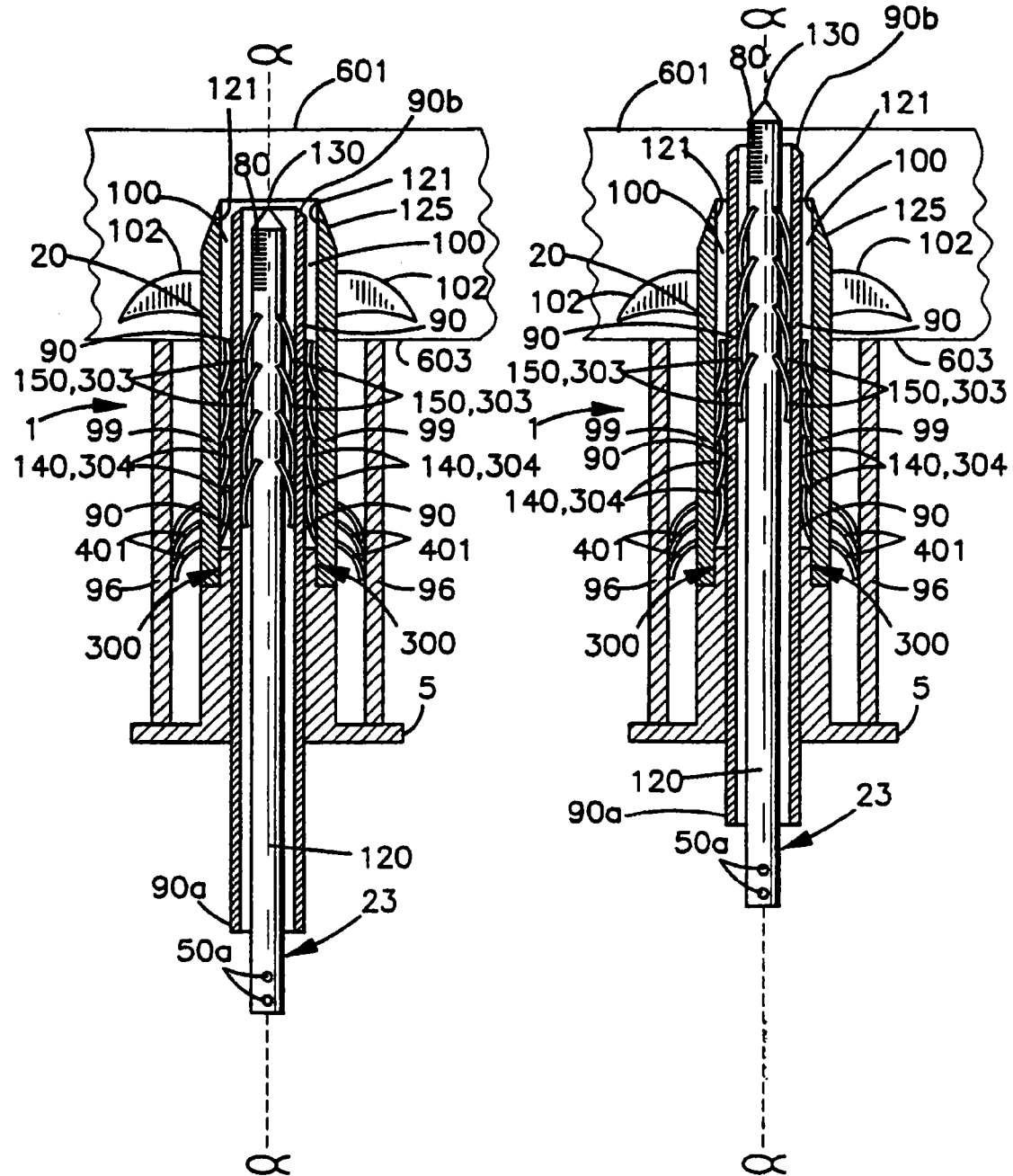
Figure 16E:
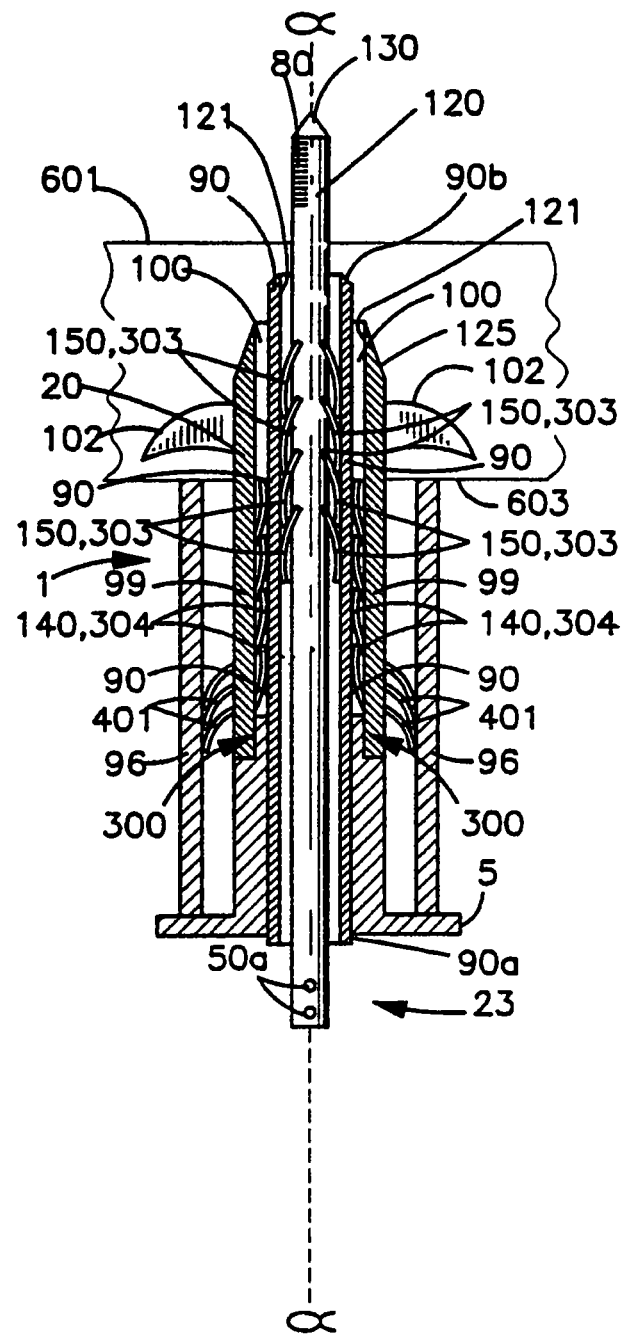

Next, shaft 120 is advanced by hand or with a hemostat, or using adjuster cylinder 90 until shaft 120 contacts the underside of skin surface 601. Adjuster cylinder 90 may comprise a cutting edge 90b for tissue penetration as shown in FIGS. 16a-16c. For instance, the adjuster cylinder 90 could be advanced over shaft 120 from below and completely through delivery device 1 until adjuster cylinder 90 advances into and punctures skin 601.

Alternatively, if shaft 120 is adapted to penetrate a tissue, shaft 120 may be advanced through skin surface 601 by moving shaft 120 upward or moving the abdominal wall downward, forcing shaft 120 through skin surface 601.

In another method, the surgeon locates the exit point of shaft 120 by pressing the abdominal wall until it contacts shaft 120 and makes a small incision with a scalpel at the exit point. By further depression of the abdominal wall, the surgeon causes shaft 120 to exit through the abdominal wall incision. The surgeon grasps and holds the protruding shaft 120 and removes pressure on the tissue and abdominal wall, thus fully deploying adjustable anchor 20. If this particular procedure is followed, shaft tip 130 need not be adapted to penetrate skin surface 601. Delivery device 1 and anchor 20 shown in FIG. 12 or 15 may deploy in this fashion.

Yet another method would be applicable with delivery device 1 having a plunger 5 adapted to activate shaft 120. In such an embodiment, shaft 120 is advanced by operation of plunger 5.

After shaft 120 passes through skin surface 601, it is held above skin surface 601, and the tension on the sutures or sling is adjusted by pulling or pushing shaft 120, using adjuster cylinder 90 to disengage the interleaving members, if needed. Once proper tension is achieved, the adjuster cylinder 90 is removed, and the interleaving members/ratcheting devices 140, 150 engage, fixing shaft 120 in place. Shaft 120 is left trailing above skin surface 601 for further postoperative adjustment.

Viewing FIG. 16a, to ease movement of shaft 120 through hollow chamber 100, ratcheting devices 140, 150 (interleaving member 303, 304) are disengaged using adjuster cylinder 90 inserted into hollow chamber 100 between shaft 120 and interior walls 121 (see FIG. 5a) of body 99. Alternatively, when shaft 120 first protrudes from the incision, adjuster cylinder 90 may be positioned through the abdominal wall (see FIG. 16g). When anchor 20 fully deploys, adjuster cylinder 90 is removed, and shaft 120 is left trailing through skin surface 601 as previously described.

An alternative procedure using a plunger-adapted delivery device 1 follows, using a two-plunger delivery device 1 shown in FIG. 13. Initially, delivery device 1 is positioned adjacent to the area to be anchored and housing 2 and hollow body portion 7 pushed upward penetrating the tissue (note the sharp end 125a of hollow body portion 7 may be adapted to penetrate a tissue). Once sharp end 125a is properly positioned for deployment of anchor 20, (generally above the surface of the penetrated tissue), the surgeon will deploy at least first plunger 301 to activate body 99, although it may be desirable to operate both plungers 301, 302. This deploys barb 102 in the soft subcutaneous tissue, superior or exterior to the rectus fascia 603 or other tissue involved. Shaft 120 is advanced by plunger 302, until shaft 120 penetrates skin surface 601. The surgeon may assist by pressing downward on the abdominal wall, thus reducing the distance that second plunger 302 must be depressed. Sharp end 125 and/or tip 130 should be adapted for tissue penetration as described.

Once shaft 120 advances through the abdominal wall, the surgeon grasps it with a hemostat. Pressure is removed from the abdominal wall, delivery device 1 is removed, and anchor 20 is fully deployed. Shaft 120 is exposed above skin surface 601 and barb 102 is set within or on the rectus fascia 603 or other appropriate tissue for later adjustment.

The surgeon may now pull (or push) on shaft 120 to raise (or lower) the attached sling until the sling is properly positioned under the bladder neck with suitable tension. Upward movement of shaft 120 may be difficult due to resistance caused by the interleaved first and second ratcheting devices, 140 and 150 (interleaving members 303, 304). When resistance is a problem, the surgeon may position adjuster cylinder 90 around shaft 120, push adjuster cylinder 90 down over shaft 120 through skin surface 601 until adjuster cylinder 90 contacts and disengages first and second ratcheting devices 140, 150 (interleaving members 303, 304) located within body 99. Adjuster cylinder 90 eases resistance. When the sling is properly tensioned, adjuster cylinder 90 is removed, allowing the first and second ratcheting devices 140, 150 (interleaving members 303, 304) to interleave, resisting movement of shaft 120 with respect to body 99 and setting the sling tension at this point. Note that it is desirable for several inches of tip 130 to protrude from the abdominal wall to assist in later adjustments. Tension adjustments may be gauged by having indicia markings 80 placed on shaft 120 (see FIGS. 16a-16h and FIG. 18b).

The exposed end of shaft 120 is taped against the abdominal wall. Postoperatively, the tension on the sling could be adjusted through the operation of the interleaved ratcheting devices 140, 150 (or interleaving members 303, 304) by adjusting the shaft 120 of the tissue anchor protruding through the abdominal skin incrementally, as described above. The patient could be brought back one to several weeks later, and the sling could be adjusted at that time in order to achieve appropriate tension minimizing urethral obstruction postoperatively. The tension is adjusted by axially pulling up or pushing down on shaft 120. Again, if too much resistance is encountered because of the interleaved ratcheting devices 140, 150 (or interleaving members 303, 304), the resistance can be eased by using adjuster cylinder 90 as described above. The tension is adjusted to the desired level, and adjuster cylinder 90 is removed, allowing ratcheting devices 140, 150 (or interleaving members 303, 304) to again interleave, resisting movement of shaft 120 relative to body 99. Anchor 20 is now once again substantially fixed in position.

The patient's progress is followed, and when a surgeon believes that appropriate tension has been placed, shaft 120 is cut below skin surface 601. This is done with a hollow needle (e.g. 21 gauge beveled) which slides down shaft 120 and cuts shaft 120 in the subcutaneous tissue at the junction with body 99, leaving anchor 20 behind with the sling at the appropriate tension. Alternatively, the exposed portion of the shaft 120 may be cut below skin surface 601 by depressing the skin around shaft 120 and cutting shaft 120. The skin is then released and recoils leaving the cut tip remote from skin surface 601.

The ability to adjust the tension postoperatively obviates the need for postoperative long-term catheterization. It also obviates the need for re-operation for obstructive uropathy by adjusting the sling postoperatively when the patient is awake and experiences normal daily activities without tissue inflammation. This gives the surgeon a realistic appraisal of the true tension that is needed for optimum correction of incontinence.

Figure 17:
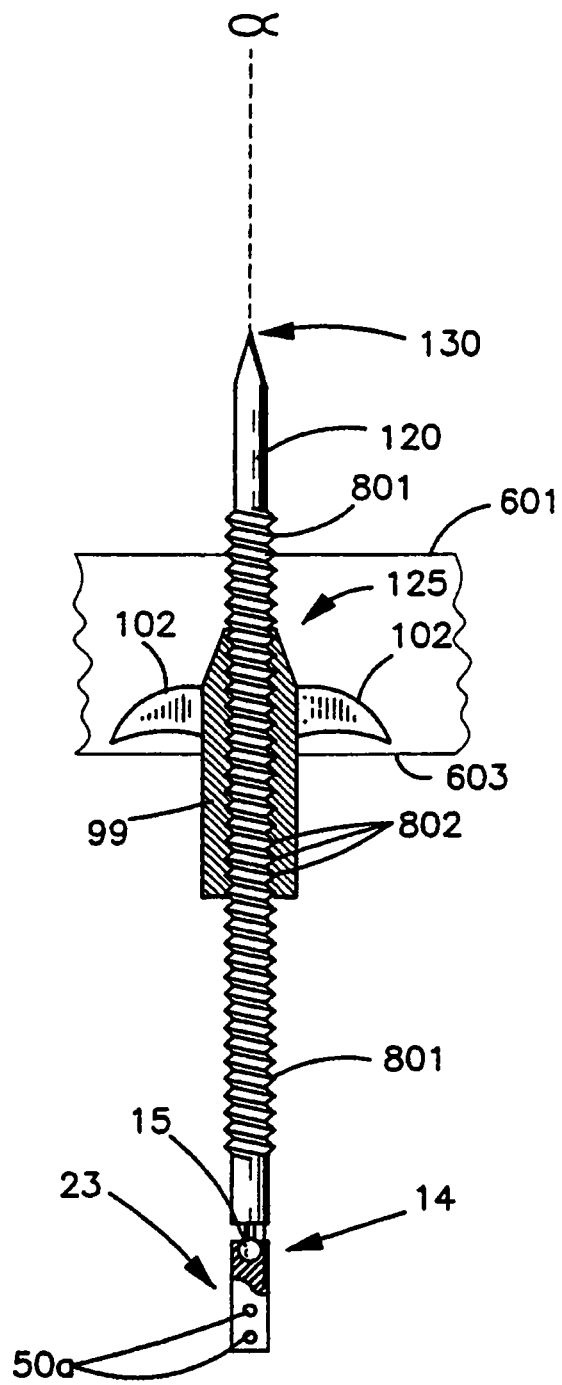
FIG. 17 illustrates a cross-sectional view of an embodiment of an adjustable anchor using threads to allow adjustment of the shaft wherein the shaft is shown in full view.

Referring to FIGS. 17 and 18c-d, adjustment of tissue or sling tension is accomplished by rotation of anchor shaft 120 clockwise or counterclockwise (for increasing or decreasing tissue tension respectively) along the 120 axial shaft. This moves shaft 120 up or down, through body 99 secured to or within tissue by the action of corresponding threads 801 on shaft 120 and threads 802 on the interior walls of body 99. After appropriate tensioning adjustments were made to shaft 120 trailing through the skin or tissue could be trimmed as previously described with the ratcheted anchor 20. FIG. 17 illustrates a similar anchor 20 to the one used in FIGS. 16a-16g, except the interleaving members on this embodiment include interleaving threads 801, 802. When using interleaving threads 801, 802, however, it is desirable that shaft 120 freely rotate while attachment member 23 does not. For this reason, attachment member 23 connects to shaft 120 using a ball and socket joint 15.

FIGS. 16a-16g illustrate a series of drawings depicting one particular embodiment of an adjustable tissue anchor 20 being positioned within a tissue. FIG. 16a illustrates anchor 20 placed against the underside of the rectus fascia 603. Delivery device 1 includes shaft 120 having first interleaving members 303 (or ratcheting devices 150) on its exterior and an attachment member 23. Shaft 120 is positioned within adjuster cylinder 90. Adjuster cylinder 90 and shaft 120 are positioned within hollow chamber 100. Hollow chamber 100 has second interleaving members 304 (or ratcheting devices 140) positioned on its interior walls 121 for interleaving with first interleaving members 303 on shaft 120. Adjuster cylinder 90 keeps first and second interleaving members 303, 304 from engaging. Barb 102 is shown as a set of deployable wings. Surrounding barbs 102 is a sleeve 96, which is slidably positioned over barbs 102 to keep barbs 102 from deploying before they insert into a tissue.

Viewing FIG. 16b, anchor 20 begins to penetrate the rectus fascia 603. The first penetration may occur by cutting edge 90b of adjuster cylinder 90, by sharp end 125 of anchor 20, or by both as shown. Viewing FIG. 16c, barb 102 penetrates the rectus fascia 603, slides through sleeve 96, which remains below the rectus fascia 603. Barb 102 advances into the subcutaneous tissue and deploys.

Viewing FIG. 16d, the surgeon pushes adjuster cylinder 90 or anchor shaft 120 to advance cylinder 90 against and through skin surface 601. Alternatively, cylinder 90 may be pressed against the underside of skin surface 601, and the surgeon then accesses cylinder 90 using an exterior incision on skin surface 601. Alternatively, tip 130 may penetrate skin surface 601. Viewing FIG. 16e, shaft 120 extends through skin surface 601 where shaft 120 has been pushed through the protruding adjuster cylinder 90 while in the position shown in FIG. 16d.

Viewing FIG. 16f, the adjuster cylinder 90 has been removed by a surgeon by withdrawing it away from skin surface 601. A button 62 has been positioned relative to shaft 120 and interleaving members 401 on shaft 120 engage interleaving members 402 in center hole 404 of button 62. The interleaving members 401, 402 affix button 62 to shaft 120. As now depicted, anchor 20 is fully set, and barbs 102 resist downward displacement. Upward displacement is resisted by button 62. Shaft 120, however, protrudes through skin surface 601 and may be pulled to increase tension, or pushed to release tension on any device attached to attachment member 23.

FIG. 16g illustrates an adjuster cylinder 90 having a funneled upper end 403. Cylinder 90 is reinserted through skin surface 601 to allow shaft 120 to be easily moved without resistance from interleaving members 303, 304. The use of the adjuster cylinder 90 in positioning of shaft 120 is optional.

Finally, shown in FIG. 20 is a long anchor shaft 120 deployed within a flexible delivery system, such as an endoscope. Generally, anchor 20 will be placed against the desired placement location, and advanced through the scope, using a rigid or flexible plunger 5 (not shown). Also shown are the video camera 65 and a screen for remote viewing of the procedure.

The terms ratcheting devices and interleaving members are used coextensively throughout. It should be noted that interleaving members may be substituted for ratcheting devices and vice versa, depending on a surgeon's desires. As used in the claims, interleaving members is intended to include ratcheting devices. In either case, ratcheting devices or interleaving members include elements that will substantially fix the position of anchor 20 or of shaft 120 positioned within anchor 20. The ratcheting devices and/or interleaving members also allow movement of anchor 20 or shaft 120 so that tension on the sling can be increased by moving shaft 120 or anchor 20 upward or decreased by moving shaft 120 or anchor 20 downward. Ratcheting devices do not exclude elements or configurations that allow shaft 120 or anchor 20 to move in multiple directions.

Although the preferred embodiment has been described, it will be appreciated by those skilled in the art to which the present invention pertains that modifications, changes, and improvements may be made without departing from the spirit of the invention defined by the claims.

The invention claimed is:

1. A method of suburethral bladder neck suspension comprising the steps of:
   a. making an incision in a patient's body to access the urethra of said patient;
   b. inserting an anchor delivery device into said incision, said anchor delivery device comprising a hand-grip and an anchor stay adapted to reversibly mate with a tissue anchor;
   c. setting a first tissue anchor positioned on said anchor delivery device into soft tissue to resist removal, said first tissue anchor located near a first side of the bladder neck, said first tissue anchor comprising (i) an anchor body having a length and barbs extending outwardly from said anchor body, said anchor body having an opening sized to accommodate an anchor shaft, (ii) an anchor shaft moveable in said anchor body opening (iii) a series of interleaving members positioned on the anchor shaft or the interior of the anchor body opening; (iv) said first tissue anchor being adapted to engage said anchor stay where said anchor body is directly attached to said first tissue; wherein said first tissue anchor is set in said first tissue to resist removal by positioning said barbs of said set anchor body into said first tissue;
   d. attaching a sling having a first end to said first tissue anchor;
   e. positioning said sling under the bladder neck; and
   f. setting a second tissue anchor connected to a second end of said sling into tissue located near a second side of the bladder neck; said second tissue anchor resisting removal from said second tissue;
   g. after said first and second tissue anchors are set to resist removal, automatically adjusting the tension in said sling: (i) to increase tension by moving said anchor shaft further into said anchor body, and (ii) to decrease tension by moving said anchor shaft further out of said anchor body.

2. The method of claim 1, wherein a portion of said anchor shaft is allowed to extend outside said body in order to allow postoperative adjustment of said anchor shaft.

3. The method of claim 1 wherein said first tissue anchor comprises a hollow body, said anchor body positioned therein when said tissue anchor is set in said first tissue.

4. The method of claim 3, wherein interleaving members are positioned on both said opening in said anchor body and said anchor shaft.

5. The method of claim 1, wherein said incision is a transvaginal incision.

6. The method of claim 1, wherein said sling is positioned at approximately a bladder neck of said patient.

7. A method of supporting a tissue comprising the steps of:
   a. making an incision in a patient's body to access the tissue to be supported;
   b. inserting a first tissue anchor into said incision, and setting said first tissue anchor into a first tissue located near said tissue to be supported, said first tissue anchor comprising (i) an anchor body having a length, said anchor body having an opening sized to accommodate an anchor shaft therethough; (ii) an anchor shaft moveable in said anchor body opening; (iii) a series of interleaving members positioned on the anchor shaft or the interior of the anchor body opening; where said tissue anchor is set in said first tissue to resist removal by attaching said anchor body directly to said first tissue;
   c. attaching a sling having a first end to said first tissue anchor;
   d. positioning said sling under said tissue to be supported;
   e. setting a second tissue anchor connected to a second end of said sling into a second tissue located near said tissue to be supported, wherein said second tissue anchor is set in said second tissue to resist removal; and
   f. after said first and second tissue anchors are set to resist removal, automatically adjusting the tension in said sling by moving said anchor shaft within said anchor body, wherein the movement of said anchor shaft further into said anchor body automatically increases tension, and wherein the movement of said anchor shaft further out of said anchor body automatically decreases tension.

8. The method of claim 7 wherein said interleaving members comprise screw threads, flexible fingers, or a ratcheting device.

9. The method of claim 7, wherein said first anchor is adjustable in order to modify tension in said sling, where said adjustment comprises moving the anchor shaft with respect to said anchor body.

* * * * *